(12) United States Patent
Lovell et al.

(10) Patent No.: US 10,184,947 B2
(45) Date of Patent: *Jan. 22, 2019

(54) SYSTEM AND METHOD FOR FLEXIBLY REPRESENTING AND PROCESSING ASSAY PLATES

(71) Applicant: Meso Scale Technologies, LLC., Rockville, MD (US)

(72) Inventors: Craig P. Lovell, Fairfax, VA (US); Thomas Lucas Hampton, III, Bristow, VA (US)

(73) Assignee: Meso Scale Technologies, L.L.C., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/468,734

(22) Filed: Mar. 24, 2017

(65) Prior Publication Data

US 2017/0199212 A1    Jul. 13, 2017

Related U.S. Application Data

(60) Continuation of application No. 13/866,187, filed on Apr. 19, 2013, which is a division of application No.
(Continued)

(51) Int. Cl.
| | | |
|---|---|---|
| *G01N 35/00* | (2006.01) | |
| *B01L 3/00* | (2006.01) | |
| *B01L 9/00* | (2006.01) | |
| *G01N 35/02* | (2006.01) | |
| *G05B 15/02* | (2006.01) | |
| *G01N 35/04* | (2006.01) | |

(52) U.S. Cl.
CPC ...... *G01N 35/00871* (2013.01); *B01L 3/5085* (2013.01); *B01L 3/545* (2013.01); *B01L 9/50* (2013.01); *G01N 35/00584* (2013.01); *G01N 35/028* (2013.01); *G05B 15/02* (2013.01); *B01L 2300/021* (2013.01); *G01N 2035/00831* (2013.01); *G01N 2035/0491* (2013.01); *Y10T 436/11* (2015.01)

(58) Field of Classification Search
None
See application file for complete search history.

(56) References Cited

U.S. PATENT DOCUMENTS

| | | |
|---|---|---|
| 5,201,046 A | 4/1993 | Goldberg et al. |
| 5,777,888 A | 7/1998 | Rine et al. |
| (Continued) | | |

*Primary Examiner* — Kathryn Wright
(74) *Attorney, Agent, or Firm* — Scully, Scott, Murphy & Presser, P.C.

(57) ABSTRACT

A flexible instrument control and data storage/management system and method for representing and processing assay plates having one or more predefined plate locations is disclosed. The system utilizes a graph data structure, layer objects and data objects. The layer objects map the graph data structure to the data objects. The graph data structure can comprise one node for each of the one or more predefined plate locations, wherein the nodes can be hierarchically defined according to a predefined plate location hierarchy. Each node can be given a unique node identifier, a node type and a node association that implements the predefined plate location hierarchy. The layer objects can include an index that maps the node identifiers to the data objects.

20 Claims, 26 Drawing Sheets

Related U.S. Application Data

10/385,924, filed on Mar. 11, 2003, now Pat. No. 8,442,689.

(60) Provisional application No. 60/363,459, filed on Mar. 11, 2002.

(56) References Cited

U.S. PATENT DOCUMENTS

| | | |
|---|---|---|
| 6,066,448 A | 5/2000 | Wohlstadter et al. |
| 6,090,545 A | 7/2000 | Wohlstadter et al. |
| 6,140,045 A | 10/2000 | Wohlstadter et al. |
| 6,200,531 B1 | 3/2001 | Liljestrand et al. |
| 6,207,369 B1 | 3/2001 | Wohlstadter et al. |
| 6,507,945 B1 | 1/2003 | Rust et al. |
| 6,673,533 B1 | 1/2004 | Wohlstadter et al. |
| 6,977,722 B2 | 12/2005 | Wohlstadter et al. |
| 7,824,925 B2 | 11/2010 | Wohlstadter et al. |
| 7,842,246 B2 | 11/2010 | Racenet et al. |
| 8,442,689 B2 | 5/2013 | Lovell et al. |
| 2002/0128734 A1 | 9/2002 | Dorsett, Jr. |
| 2002/0128993 A1 | 9/2002 | Jevons et al. |
| 2004/0033610 A1 | 2/2004 | Lovell et al. |
| 2004/0072195 A1 | 4/2004 | Hunkapiller et al. |
| 2005/0182775 A1 | 8/2005 | Fitzgerald et al. |
| 2013/0238134 A1 | 9/2013 | Lovell et al. |

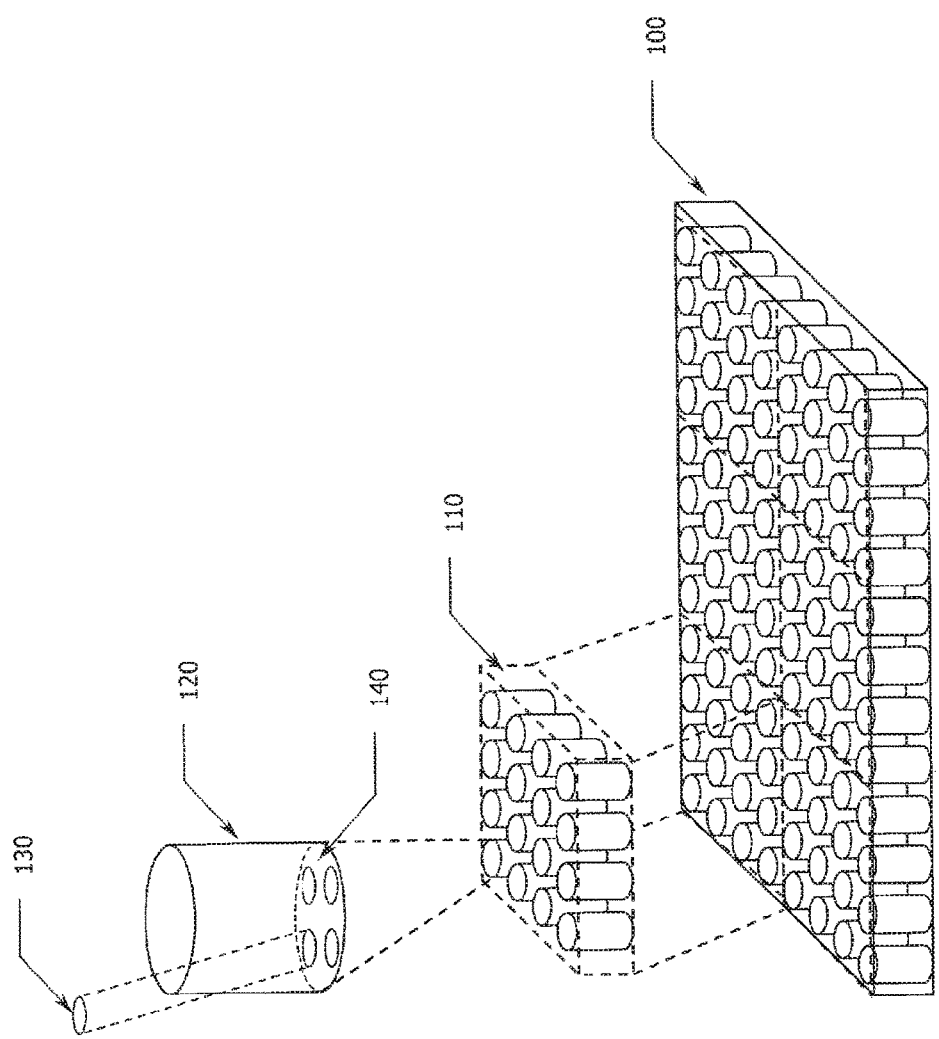

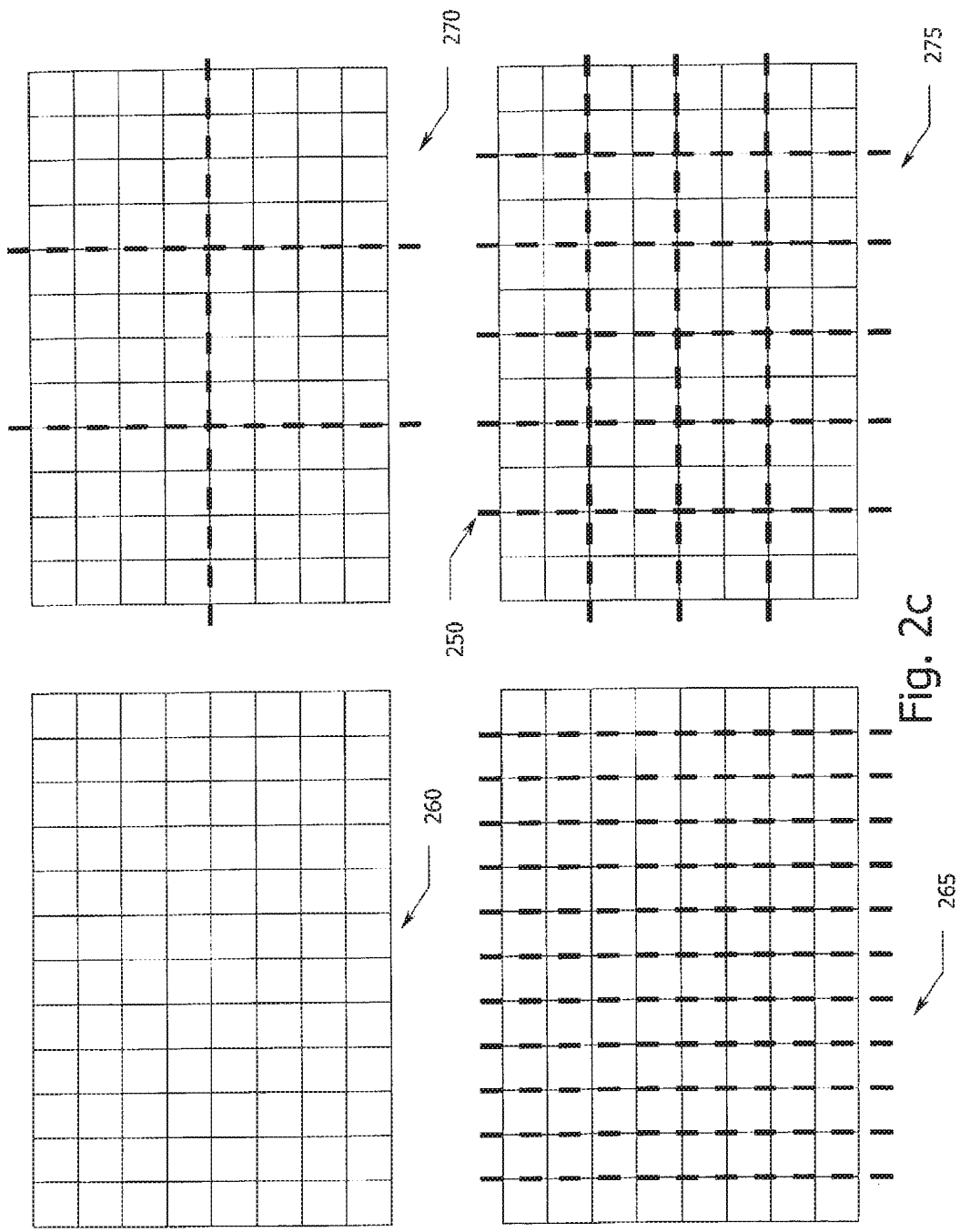

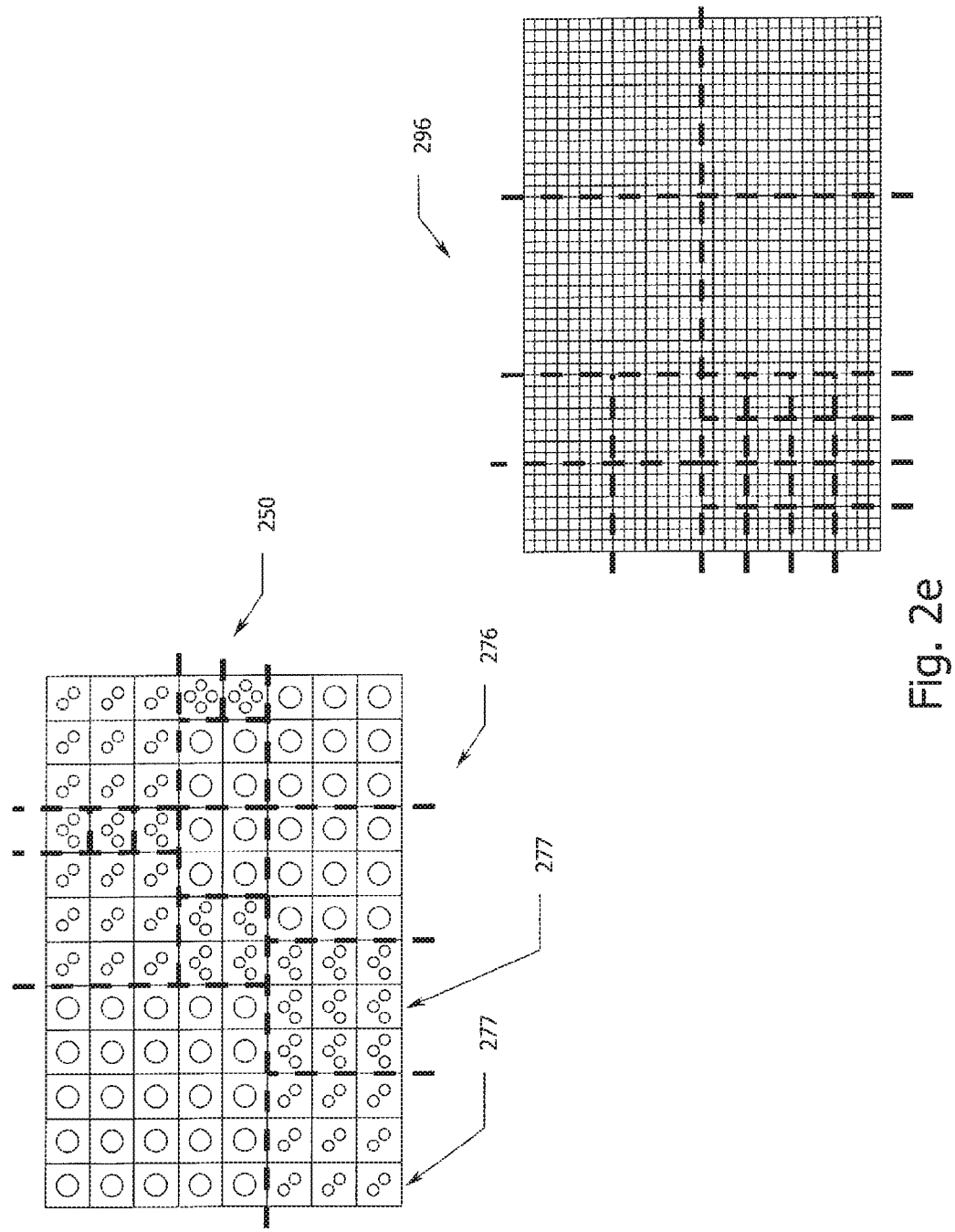

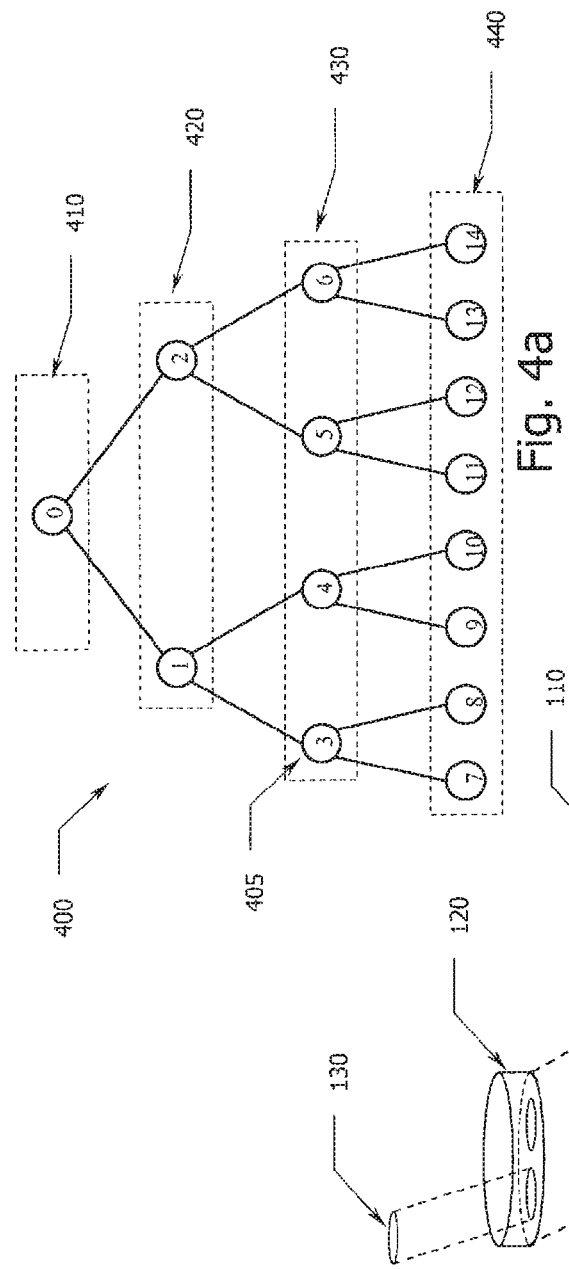
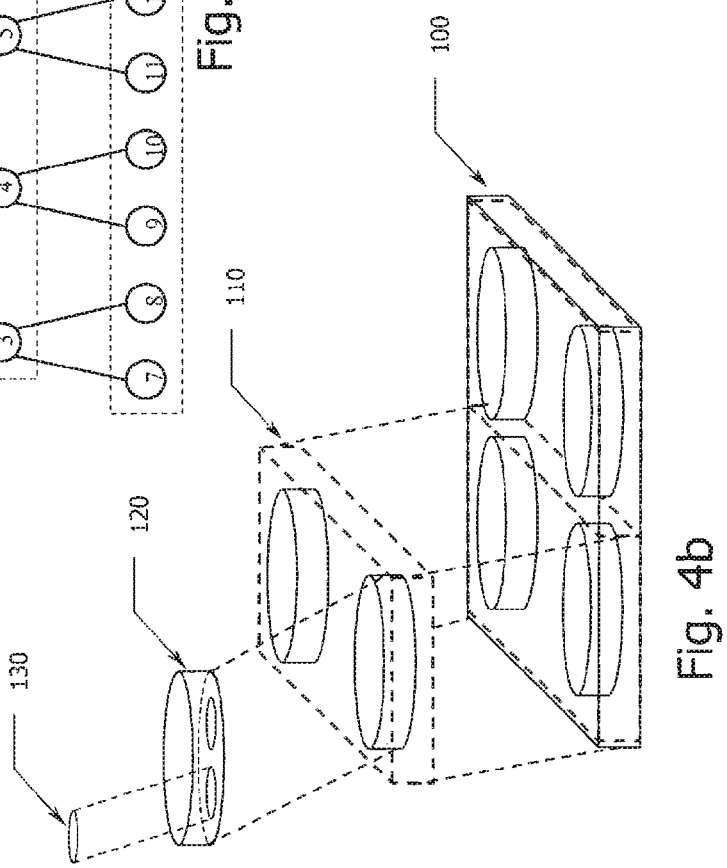

Fig. 5a

| plateTypeInfoID | name | desc | height | wellShape | type | maxVol | numSpots | numSectorRows | numSectorColumns | numWellRows | numWellColumns | spaceID | graphID |
|---|---|---|---|---|---|---|---|---|---|---|---|---|---|
| 1 | "4W2S" | "4-Well 2-Spot Plate" | 12 | FLAT | 4 | 350 | 2 | 1 | 2 | 2 | 2 | 2 | 3 |
| 2 | "4W4S" | "4-Well 4-Spot Plate" | 14 | ROUND | 5 | 380 | 4 | 4 | 4 | 2 | 2 | 3 | 4 |

Fig. 5b

| plateTypeInfoID | barCodePlateType |
|---|---|
| 1 | 4 |
| 1 | 4 |
| 2 | 5 |

Fig. 5c

| plateTypeInfoID | instrumentModel |
|---|---|
| 1 | "SectorHTS" |
| 2 | "SectorHTS" |

Fig. 5d

| graphID | name |
|---|---|
| 3 | "4W2SGraph" |
| 4 | "4W4SGraph" |

Fig. 5m

| REGISTRY FILE | |
|---|---|
| PlateTypeID = | 5 |
| DataPopulation = | HTS96W1SPopulate.class |
| SaturationDetection = | HTS96W1SImageProcessor.class |
| CrosstalkCorrection = | HTS96W1SImageProcessor.class |
| CenterSearch = | HTS96W1SImageProcessor.class |
| MaskCreation = | HTS96W1SImageProcessor.class |
| ImagePrepare = | HTS96W1SImageProcessor.class |
| LayoutGraph = | type5graph.ser |
| AdjustResult = | GainCalculator.class |
| BarCodeParser = | HTS96W1SbarCodeParser.class |
| SpotRenderer = | Round1SpotRenderer.class |

| graphID | locationID | parentLocationID | locationType |
|---|---|---|---|
| 3 | 0 | NULL | PLATE |
| 3 | 1 | 0 | SECTOR |
| 3 | 2 | 0 | SECTOR |
| 3 | 3 | 1 | WELL |
| 3 | 4 | 1 | WELL |
| 3 | 5 | 2 | WELL |
| 3 | 6 | 2 | WELL |
| 3 | 7 | 3 | SPOT |
| 3 | 8 | 3 | SPOT |
| 3 | 9 | 4 | SPOT |
| 3 | 10 | 4 | SPOT |
| 3 | 11 | 5 | SPOT |
| 3 | 12 | 5 | SPOT |
| 3 | 13 | 6 | SPOT |
| 3 | 14 | 6 | SPOT |
| 4 | 0 | NULL | PLATE |
| 4 | 1 | 0 | WELL |
| 4 | 2 | 0 | WELL |
| 4 | 3 | 0 | WELL |
| 4 | 4 | 0 | WELL |
| 4 | 5 | 1 | SECTOR |
| 4 | 6 | 1 | SECTOR |
| 4 | 7 | 1 | SECTOR |
| 4 | 8 | 1 | SECTOR |
| 4 | 9 | 2 | SECTOR |
| 4 | 10 | 2 | SECTOR |
| 4 | 11 | 2 | SECTOR |
| 4 | 12 | 2 | SECTOR |
| 4 | 13 | 3 | SECTOR |
| 4 | 14 | 3 | SECTOR |
| 4 | 15 | 3 | SECTOR |
| 4 | 16 | 3 | SECTOR |
| 4 | 17 | 4 | SECTOR |
| 4 | 18 | 4 | SECTOR |
| 4 | 19 | 4 | SECTOR |
| 4 | 20 | 4 | SECTOR |
| 4 | 21 | 5 | SPOT |
| 4 | 22 | 6 | SPOT |
| 4 | 23 | 7 | SPOT |
| 4 | 24 | 8 | SPOT |
| 4 | 25 | 9 | SPOT |
| 4 | 26 | 10 | SPOT |
| 4 | 27 | 11 | SPOT |
| 4 | 28 | 12 | SPOT |
| 4 | 29 | 13 | SPOT |
| 4 | 30 | 14 | SPOT |
| 4 | 31 | 15 | SPOT |
| 4 | 32 | 16 | SPOT |
| 4 | 33 | 17 | SPOT |
| 4 | 34 | 18 | SPOT |
| 4 | 35 | 19 | SPOT |
| 4 | 36 | 20 | SPOT |

Fig. 5e

| plateLayoutID | name | desc | version | rootVersionID | ownerName | isPublic | timestampData | plateTypeInfoID |
|---|---|---|---|---|---|---|---|---|
| 4 | "Standard" | "Default 4-Well 2-Spot Layout" | 1 | 4 | "J. Smith" | TRUE | 1/1/2001 12:00 | 1 |
| 5 | "Standard" | "Default 4-Well 4-Spot Layout" | 1 | 5 | "J. Smith" | TRUE | 3/1/2002 15:50 | 2 |
| 6 | "Standard" | "4-Well 2-Spot long waveform test" | 1 | 6 | "R. Jones" | FALSE | 3/3/2002 12:39 | 1 |

Fig. 5f

| plateID | comment | ownerName | isPublic | manufacturerBarCode | customerBarCode | orientation | timestampData | instrumentSerialNumber | plateLayoutID |
|---|---|---|---|---|---|---|---|---|---|
| 20 | "Monday's Test Plate" | "J. Smith" | FALSE | "*4351365004V*" | "10045" | FORWARD | 2/25/2002 13:05 | "HTS-CS434" | 4 |
| 21 | "Tuesday's Test Plate" | "J. Smith" | FALSE | "*4351365005V*" | "10046" | REVERSE | 2/26/2002 10:15 | "HTS-CS434" | 4 |
| 22 | "Wednesday's Test Plate" | "J. Smith" | FALSE | "*4351365006V*" | "10047" | FORWARD | 2/27/2002 11:03 | "HTS-CS434" | 4 |
| 23 | "AFP Assay" | "R. Jones" | TRUE | "*5351365006V*" | "12201" | FORWARD | 3/1/2002 15:53 | "HTS-CS434" | 5 |
| 24 | "Partial waveform test" | | FALSE | "*5351365006V*" | "12205" | FORWARD | 3/3/2002 12:41 | "HTS-CS434" | 6 |

Fig. 5h

| plateID | layerID |
|---|---|
| 20 | 11 |
| 20 | 12 |
| 21 | 13 |
| 21 | 14 |
| 22 | 15 |
| 22 | 16 |
| 23 | 18 |
| 23 | 19 |

Fig. 5i

| plateLayoutID | layerID |
|---|---|
| 4 | 10 |
| 5 | 17 |
| 6 | 20 |

Fig. 5g

| layerID | name |
|---|---|
| 10 | "DetectionParameters" |
| 11 | "Results" |
| 12 | "ReadContext" |
| 13 | "ReadContext" |
| 14 | "Results" |
| 15 | "ReadContext" |
| 16 | "Results" |
| 17 | "DetectionParameters" |
| 18 | "Results" |
| 19 | "ReadContext" |
| 20 | "DetectionParameters" |

Fig. 5j

| layerID | locationID | layerData |
|---|---|---|
| 10 | 1 | <Detection parameter id1> |
| 10 | 2 | <Detection parameter id1> |
| 11 | 7 | <Result 1> |
| 11 | 8 | <Result 2> |
| 11 | 9 | <Result 3> |
| 11 | 10 | <Result 4> |
| 11 | 11 | <Result 5> |
| 11 | 12 | <Result 6> |
| 11 | 13 | <Result 7> |
| 11 | 14 | <Result 8> |
| 12 | 0 | <Read Context 1> |
| 13 | 7 | <Result 9> |
| 13 | 8 | <Result 10> |
| 13 | 9 | <Result 11> |
| 13 | 10 | <Result 12> |
| 13 | 11 | <Result 13> |
| 13 | 12 | <Result 14> |
| 13 | 13 | <Result 15> |
| 13 | 14 | <Result 16> |
| 14 | 0 | <Read Context 2> |
| 15 | 7 | <Result 17> |
| 15 | 8 | <Result 18> |
| 15 | 9 | <Result 19> |
| 15 | 10 | <Result 20> |
| 15 | 11 | <Result 21> |
| 15 | 12 | <Result 22> |
| 15 | 13 | <Result 23> |
| 15 | 14 | <Result 24> |
| 16 | 0 | <Read Context 3> |
| 17 | 5 | <Detection parameter id2> |
| 17 | 6 | <Detection parameter id2> |
| 17 | 7 | <Detection parameter id2> |
| 17 | 8 | <Detection parameter id2> |
| 17 | 9 | <Detection parameter id2> |
| 17 | 10 | <Detection parameter id2> |
| 17 | 11 | <Detection parameter id2> |
| 17 | 12 | <Detection parameter id2> |
| 17 | 13 | <Detection parameter id2> |
| 17 | 14 | <Detection parameter id2> |
| 17 | 15 | <Detection parameter id2> |
| 17 | 16 | <Detection parameter id2> |
| 17 | 17 | <Detection parameter id2> |
| 17 | 18 | <Detection parameter id2> |
| 17 | 19 | <Detection parameter id2> |
| 17 | 20 | <Detection parameter id2> |
| 18 | 21 | <Result 25> |
| 18 | 22 | <Result 26> |
| 18 | 23 | <Result 27> |
| 18 | 24 | <Result 28> |
| 18 | 25 | <Result 29> |
| 18 | 26 | <Result 30> |
| 18 | 27 | <Result 31> |
| 18 | 28 | <Result 32> |
| 18 | 29 | <Result 33> |
| 18 | 30 | <Result 34> |
| 18 | 31 | <Result 35> |
| 18 | 32 | <Result 36> |
| 18 | 33 | <Result 37> |
| 18 | 34 | <Result 38> |
| 18 | 35 | <Result 39> |
| 18 | 36 | <Result 40> |
| 19 | 0 | <Read Context 4> |
| 20 | 1 | <Detection Parameter id3> |

Fig. 5k

SYSTEM AND METHOD FOR FLEXIBLY REPRESENTING AND PROCESSING ASSAY PLATES

CROSS REFERENCE TO RELATED APPLICATIONS

The present application is a continuation of copending application Ser. No. 13/866,187, filed on Apr. 19, 2013, which is a divisional of application Ser. No. 10/385,924, filed on Mar. 11, 2003, now U.S. Pat. No. 8,442,689, which claims the benefit of U.S. Provisional Application No. 60/363,459, filed Mar. 11, 2002, the disclosures of which are incorporated herein by reference in their entirety.

FIELD OF THE INVENTION

The present invention relates generally to software architecture and design; more particularly, to a system and method for flexibly representing and processing assay plates.

BACKGROUND OF THE INVENTION

Microtiter plates are used in many chemical, biochemical and biological processes ranging from simple chemical reactions and/or compound synthesis to analytical testing. Microtiter plates can come in various shapes, sizes and configurations. In certain instances the configuration of commercially available microtiter plates has undergone standardization. For example, the Society for Biomolecular Screening (SBS) has published recommended microtiter plate specifications for a variety of plate formats. These published standards set forth, inter alia, various requirements for length, width, depth, well geometry, well spacing, and form factor. Microtiter plates manufactured in accordance with these standards are assured to have certain dimensions and physical characteristics that allow users to design instruments, tests and procedures that can reliably use such standardized microtiter plates. Industry standards such as those published by the SBS ensure interchangeability and compatibility and allow automated handling. Recently, commercial manufacturers of equipment for processing and analyzing samples in multi-well plates have begun selling equipment that is capable of handling more than one plate type. It is readily understood that many of these instruments need to adjust their operation depending on the type of plate being handled.

Commonly assigned U.S. Pat. Appln. No. 60/301,932, incorporated herein by reference in its entirety, discloses specialized microtiter plates that, preferably, adhere to the physical specifications of certain SBS standards. These specialized plates are, preferably, capable of being used with any automated plate handling system that adheres to the same SBS standards.

In preferred embodiments of the 60/301,932 application, specialized plates are disclosed that are suitable for use in specialized electrochemiluminescence-based assays and instruments. These specialized plates can be configured in many different ways, differing in the number of wells (96, 384, 1536 etc.), in the height of the well/plate (standard or deep-well), or in the well bottom shape (flat, round, conical, etc.). A further physical difference in the configuration of these specialized plates relates to the plate bottoms. The plate bottoms differ from standardized assay plates in that there may be patterns of electrodes on these plate bottoms. The electrodes may typically be arranged on the plate bottom such that each electrode may span one or more wells and/or such that each well spans one or more electrodes. These electrodes may be used for inducing electrochemiluminescence (ECL) reactions within the well that are designed to measure a particular analyte of interest. ECL is induced by stimulating, i.e., supplying electrical energy to, one or more electrodes within a well. Still further, some of these specialized plates incorporate binding reagents immobilized on the working electrodes found in the wells. Each well can contain a number of these binding reagents, referred to as spots or binding domains, in a number of different arrangements, or layouts. A single well containing a number of these distinct binding domains, or spots, is capable of testing a single sample for a number of different analytes of interest (typically, one analyte for each spot).

In certain instances, these specialized plates use groupings, or regions referred to as sectors, of electrodes located on the plate bottoms to simultaneously induce electrochemiluminescence in the wells having the grouped electrodes. Such sectors may be the result of physical groupings, (e.g., a group of electrodes that are electrically connected through leads on the plate bottom) or may be the result of the instrument stimulating more than one physically distinct electrode simultaneously. In any case, the number and layout of sectors across a plate can depend on the type of instrument to be used to process the plate. For example, one instrument could process a 96-well plate by stimulating a single column of the plate; i.e., a column of 8 wells at a time. In this instance, the plate could be divided into 12 sectors, each sector containing 8 wells. Yet another instrument may use a 2×3 grid of sectors partitioning a 96 well plate into 6 sectors of 16 wells each. Still yet another instrument could have multiple sectors inside each well wherein each sector represents an individually addressable electrode. In this instance the individual addressable electrode may also define a binding domain or spot. As is described in more detail in the application Ser. No. 06/301,932, the grouping of electrodes and/or wells into sectors provides certain advantages in the analysis of luminescence emitted from a plate when compared to the simultaneous measurement of luminescence from whole plates or the serial detection of luminescence from each individual well. U.S. Pat. No. 6,200,531 (hereby incorporated by reference) discloses instruments that use fluidics to move samples from a plate to be assayed into a separate vessel or chamber where the analysis takes place. In such a fluidics-based instrument, a hollow probe or pipette that is lowered into the well may, be used to aspirate the sample and transfer it into the special vessel or chamber for testing. It is readily apparent then that the dimensions and configuration of the plate will determine the probe depth and motion profiles.

Past attempts at enabling instruments to process various plate types and/or various plate configurations coded the instrument control software with all of the requisite information for each anticipated plate type. However, such an approach requires that all anticipated plate types be known and sufficiently defined so that the instrument control software may be properly coded. Such an approach is difficult, time consuming and inflexible and would require significant software recoding to implement/deploy newly devised plate types. Furthermore, such an approach would more than likely entail recoding the system software as well as recoding the software's representation of a particular plate type.

Therefore, a need exists for flexible software architecture and designs for managing plate data and for supporting field deployable plate types. Such an architecture must be capable of accounting for differences in the plate type configurations (e.g., number and arrangement of wells, sectors and spots; well height and shape; electrode contact configuration; etc.) in addition to different instruments (e.g., ECL-based instruments utilizing specialized plates with different sector, well and spot layouts; fluidics-based instruments; etc.).

SUMMARY OF THE INVENTION

When developing software to control automated instrumentation for manipulating or analyzing multi-well plates, one possible approach is to develop separate motor controlling routines, data structures, graphical representations, analysis routines, etc. for each plate type. While this approach is the simplest in concept, as the number of plate types increases so does the complexity of the software, the number of lines of code and the use of memory. In addition, this approach does not allow the instrumentation to handle additional plate types without altering the software.

By contrast, the current invention associates with a given plate type a set of parameters that specify the characteristics of that plate type. This set of parameters may be small or large depending on the range of plate types that a particular instrument is expected to handle and may encompass the geometry or physical properties of the plate as well as the number, arrangement, size, shape, physical properties, etc. of sectors, wells, spots, etc. defined within the plate. Preferably, the software is sufficiently generalized so that it may use the set of parameters associated with a plate to create the appropriate motor controlling routines, data structures, graphical representations, analysis routines, etc. for that plate type. In cases where a new plate type requires a more substantial change to an algorithm coded by the software, the software, preferably, supports update modules containing both static data and algorithms

BRIEF DESCRIPTION OF THE DRAWINGS

FIG. 1a illustrates one example of the plate regions on a 96-well plate, and the containment relationships of the plate to its sectors, a sector to its wells and a well to its spots.

FIG. 1b illustrates an alternative configuration having containment relationships that differ from FIG. 1a.

FIG. 2c illustrates four possible containment relationships for a 96-well plate.

FIG. 2e illustrates multi-well plates having multiple containment relationships on a single plate.

FIG. 4a illustrates a simple tree data structure representation of the plate in FIG. 4b that was constructed according to the UML representation of FIG. 3.

FIG. 4b illustrates a four-well, 2-spot assay plate as represented by the tree data structure of FIG. 4a.

FIGS. 5a through 5k illustrate example contents of the database schema shown in FIG. 5.

FIG. 5m illustrates a property file for deploying new plate types.

DETAILED DESCRIPTION

Figure 1B:
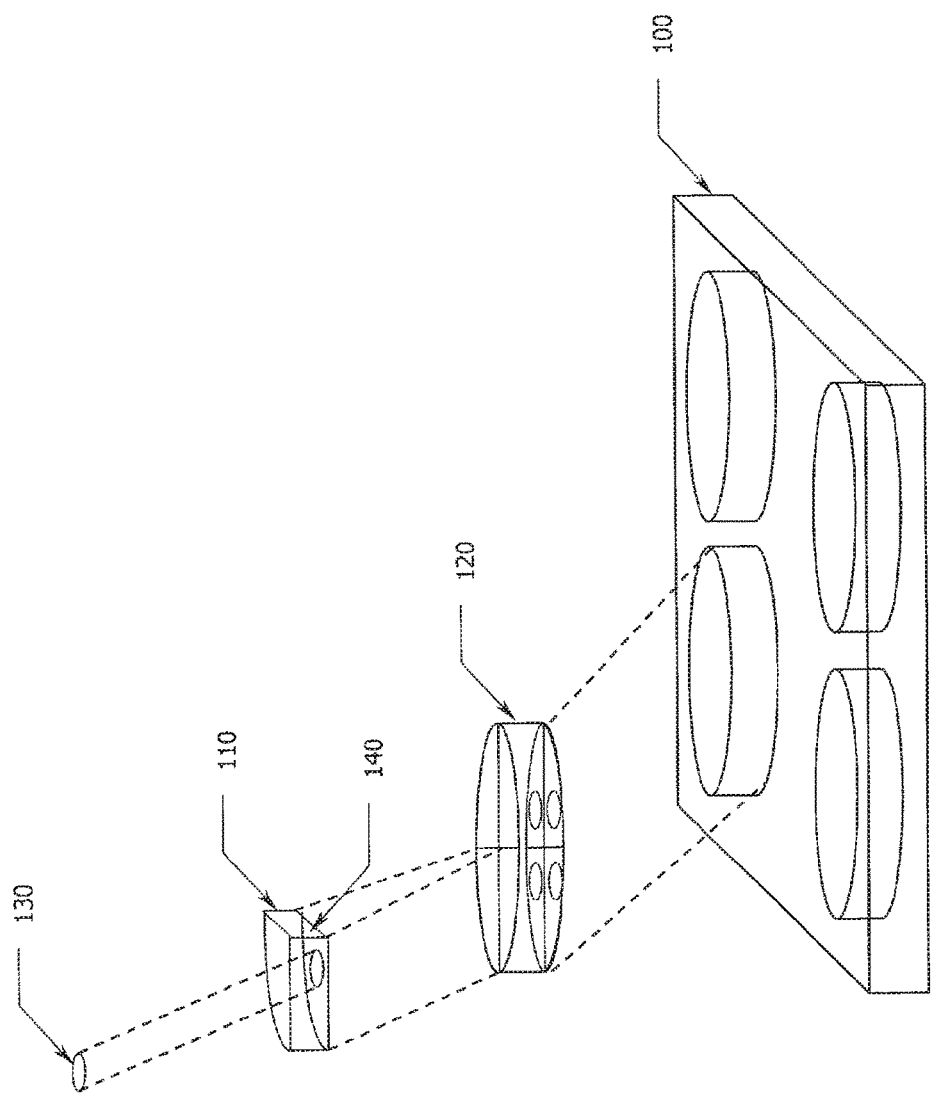

The invention, as well as additional objects, features and advantages thereof, will be understood more fully from the following detailed description of certain preferred embodiments.

Multi-well plates that may be represented by the systems and methods of the invention include any plates that can be described by a characteristic set of parameters. Preferred plates include plates having rectangular arrays of wells (e.g., 2n×4n, 3n×9n, etc.), more preferably having an array of 2n×3n wells where n is an integer, most preferably a power of two. Examples include 6 well, 24 well, 96 well, 384 well, 1536 well, 6144 well and 9600 well plates. Especially preferred plate types include plates that meet the standards of the Society for Biomolecular Screening (SBS) for plate dimensions and for the arrangement of wells. Plates may have other properties or features associated with them that may be desirable for specific applications, e.g.: a) well shape and dimensions (e.g., round, square, flat bottom, round bottom, conical bottom, shallow well, deep well, etc.); b) opacity of well bottom and/or the sides of the wells (e.g., the inner surfaces of the well may be clear, light absorbing, light reflecting, light scattering, etc.; in some plates the well bottoms and well sides may differ in optical properties); c) functional elements (e.g., scintillant containing material for carrying out radioactivity based assays or electrodes for carrying out electrochemical or electrochemiluminescent assays, d) plate composition (e.g., polystyrene, polypropylene, glass, quartz, etc.), e) surface treatments (e.g., adsorbed layers of assay reagents or surface treatments designed to enhance or prevent adsorption of biomolecules) and f) patterns or arrays of one or more assay reagents or assay domains within a well (e.g., a patterned array of assay reagents deposited on the well bottom of one or more wells within a plate). One or more of these parameters (including the location, amount and identity of assay reagents) may be important in optimizing the way a specific instrument handles a specific plate type.

In this specification, inventive concepts may be disclosed in the context of assay plates (e.g., electrode configuration, wells, spots, sectors, etc.), however, the concepts are also applicable to other assay modules, including cartridges, cassettes, dip sticks, and the like (see U.S. Appln. No. 60/301,932).

Instruments that may benefit from the methods of the invention include instruments that process or analyze samples in multi-well plates, e.g., a) systems for storing or incubating plates, b) systems for moving plates (e.g., robotic systems), c) systems for dispensing fluids and/or aspirating fluids from plates (e.g., fluid dispensers and plate washers) and systems for performing analyses on samples in the wells of a plate (e.g., readers for measuring properties of a sample in a plate including: optical absorbance, fluorescence, chemiluminescence, light scattering, magnetism, radioactivity, electrochemiluminescence, conductivity, capacitance, temperature, electrochemical properties, etc.). Such measurements may be carried out while the sample is in the plate or may involve transfer of the sample to a separate container or flow cell.

Multi-well plates normally have plate regions/locations that are logically and/or physically defined. FIG. 1a is a simplified depiction of a multi-well plate 100 using a plate body that conforms to the standard 96-well assay plate. Also depicted are the various plate regions/locations that may be prescribed, or predefined, on such a specialized plate. The assay plate 100 of FIG. 1a has a total of six sectors 110, where each sector contains sixteen wells 120 and each well 120 contains four spots 130 defined on a surface of the well. In certain preferred embodiments, the well may, optionally, include an electrode 140 on which the spots are defined.

A spot is preferably a region defined within a single well; e.g., a spot may be defined by immobilized assay reagents or by passivation of certain areas on the electrode. Different assay reagents immobilized to the bottom of a single well allow a single sample in that well to be assayed for a number of different analytes (once for each spot). Each well can contain a number of these bindings/spots.

In certain preferred embodiments, a sector may be defined as a region of the assay plate that is processed simultaneously by an assay instrument. In such a simultaneously processed sector embodiment, a sector need not be a contiguous area on the assay plate; e.g., a sector may include two or more areas of the plate that are contiguous within themselves but that are physically separated from one another by other areas of the plate. Furthermore, a simultaneously processed sector is processed when the one or more areas comprising the sector are simultaneously stimulated and/or sensed. The present invention, however, is not necessarily limited to embodiments that prescribe some functional significance to a sector. The division of plate into sectors may reflect an inherent physical property of a plate (e.g., a series of wells having electrodes that are controlled by a single common lead), it may be a consequence of the geometry of a plate processing instrument (e.g., in describing the relationship of a 96 well plate to an eight channel fluid dispenser or an optical plate reader having an array of eight photodiodes, it may be advantageous to describe the plate as having 12 sectors of 8 wells), or it may simply be an arbitrarily defined notion, prescribed by the user (e.g., a user may define a plate as being divided into a test sector and a calibration sector).

Figure 1C:
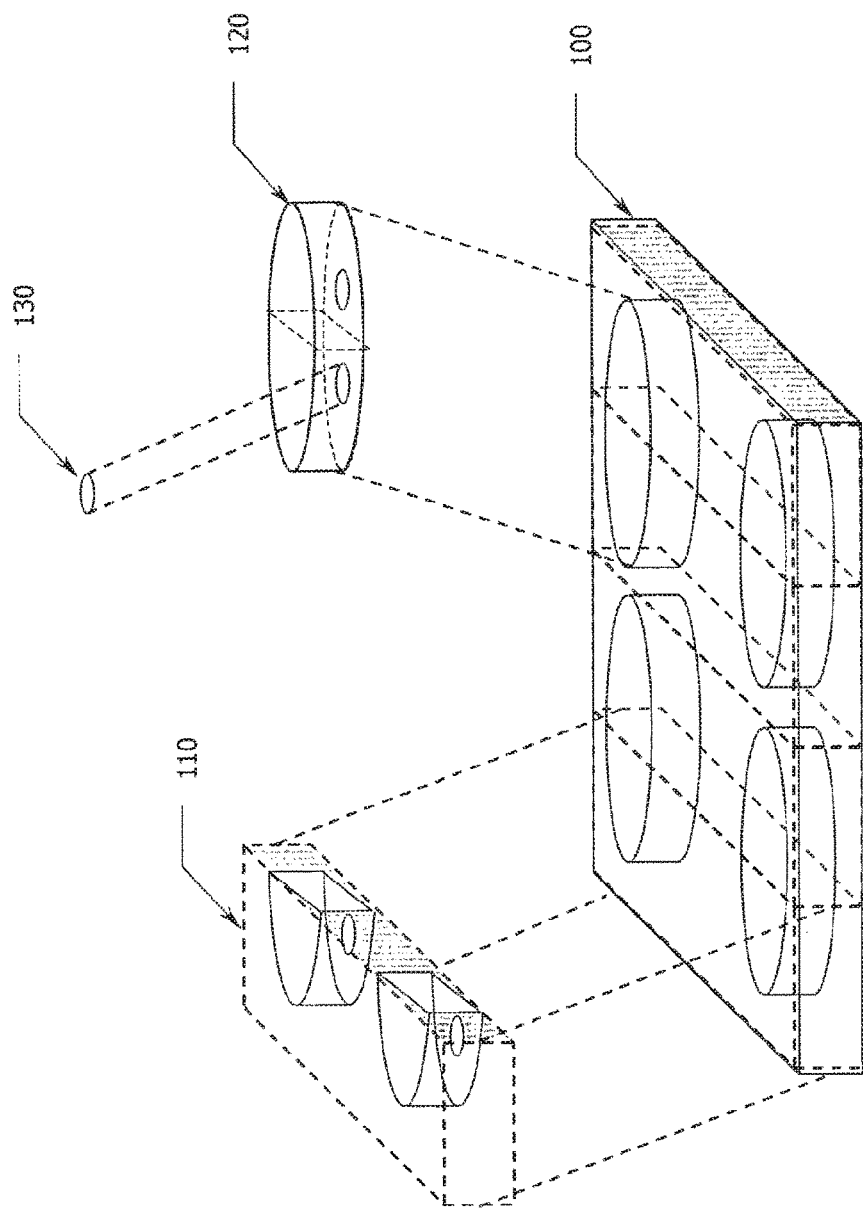
FIG. 1c illustrates an alternative configuration having containment relationships that overlap.

FIG. 1a depicts certain illustrative containment relationships. Plate 100 contains sectors 110; the sectors 110 contain wells 120; and the wells 120 contain spots 130. These containment relationships define a hierarchy of spots to wells, wells to sectors and sectors to a plate, however, certain alternative configurations may yield different containment relationships and therefore a different hierarchy. FIG. 1b illustrates one possible alternative configuration of an assay plate 100 where a well 120 contains sectors 110 and the sectors 110 contain spots 130. In certain preferred embodiments, the sector may, optionally, include an electrode 140 on which a spot is defined. In FIG. 1b, each of the spots 130 can be individually processed, e.g., if electrodes 140 are individually addressable. Therefore, as illustrated in FIG. 1b, a single well 120 can contain multiple sectors 110. FIG. 1c illustrates another alternative configuration of an assay plate 100 that contains wells 120 and sectors 110. In FIG. 1c wells 120 contain spots 130 and sectors 110 contain spots 130. Therefore, as illustrated in FIG. 1c, a spot 130 may be contained by more than one graph node.

In preferred embodiments of the invention, the methods, apparatus and systems of the invention are adapted so as to allow the handling, processing and analysis of plates having integrated electrodes and, in particular, the specialized plates described in U.S. Provisional Pat. Appln. No. 60/301,932 for use in ECL-based assays. The 60/301,932 application provides a thorough discussion of the specific details of these specialized plates. These specialized plates may be referred to, herein, as ECL plates, although, it is understood that their utility may extend to non-ECL based assays including assays based on measurements of photoluminescence, chemiluminescence, voltametry, amperometry, and the like. In one embodiment of the invention, assay plate 100 of FIG. 1a is configured to induce and measure ECL-based assays and includes electrodes 140; the wells 120 contained in sector 110 are simultaneously analyzed by applying an appropriate electrical signal to the electrode 140 that forms the bottom of each well 120 and detecting the luminescence emitted from each spot 130 within each well 120.

In certain embodiments, a sector of an ECL plate may be defined physically through predefined electrical interconnections of the electrodes in each well. In other embodiments, such as for example when two or more electrodes or groups of electrodes are individually addressable, the two or more electrodes or groups of electrodes are separately, but simultaneously, addressed by the circuitry of the instrument. In such an instance, two or more electrical contacts, or one electrical contact with multiple contact points, may be used to simultaneously address the two or more electrodes or groups of electrodes.

Figure 2A:
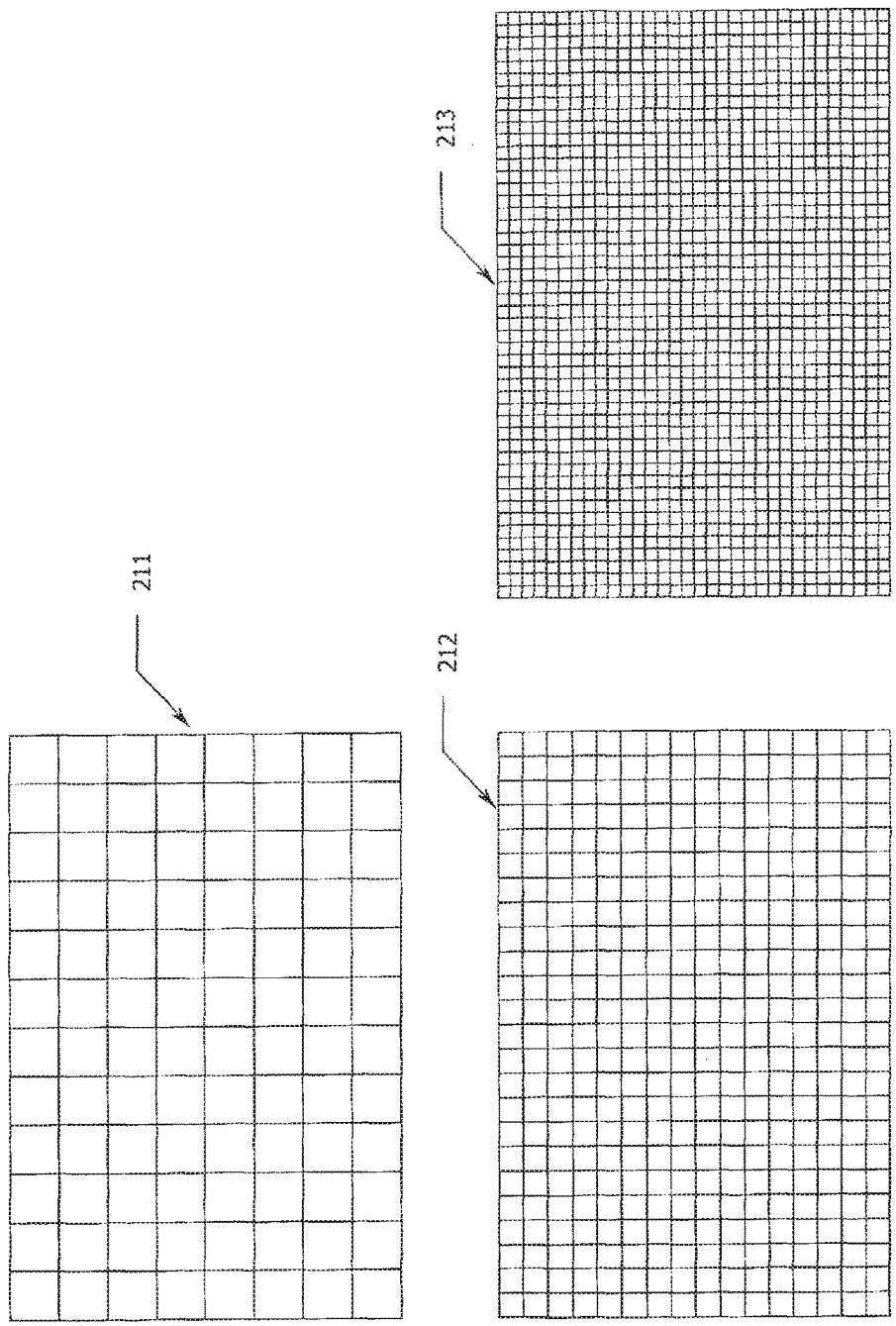
FIG. 2a illustrates standard plate bodies for 96, 384 and 1536-well plates.
Figure 2B:
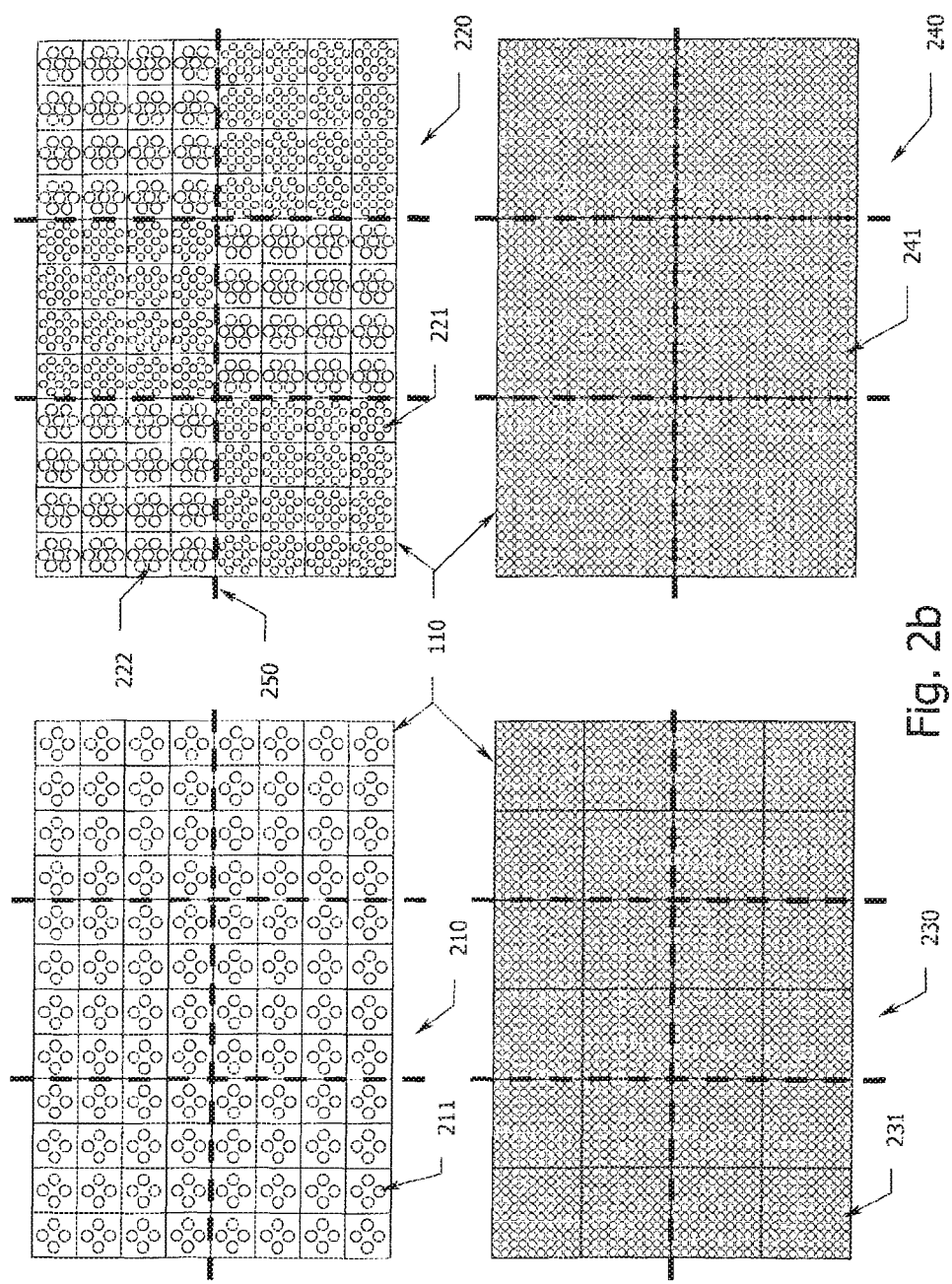
FIG. 2b illustrates four specialized plate configurations and their respective containment relationships.

FIG. 1a depicts only one possible configuration of a 96-well assay plate. However, many different assay plate configurations are in wide use today. For example, FIG. 2a illustrates three of these widely used standard multi-well assay plate configurations: 96-well 211; 384-well 212; and 1536-well 213 (for simplicity the wells are depicted as square shaped wells but it should be understood that the wells can be shaped in any number of geometrical configurations; e.g., round, oval, triangular, rectangular, etc.). FIG. 2b illustrates four plates that have an identical sector region layout but differing well and/or spot layouts. The heavy dashed lines 250 in FIG. 2b delineate the sector regions of the plate. As illustrated, various configurations are possible even when an identical sector layout may be employed.

Plates 210 and 220 have identical sector layouts 250 and identical well layouts 110 but differing spot layouts 211, 221, 222; plate 210 has a 4-spot layout 211 per well 110 whereas plate 220 has both 7-spot 222 and 12-spot 221 layouts per well 110. Moreover, plate 220 differs from plate 210 not only in that the respective spot layouts are different from plate to plate but also in that plate 220 has non-uniform spot layouts across the plate; i.e., plate 220 has differing spot layouts from sector to sector 221, 222. In fact, an alternative plate (not shown) may even have differing spot layouts within a single sector. Plate 230 shows another possible configuration having the same 6 sectors 250 but only 4 wells 110 per sector 250 and 100 spots 231 per well 110. Still another configuration depicted by plate 240 has the same 6 sectors 250 but only one well 110 per sector 250 and 400 spots 241 per well 110.

Figure 2D:
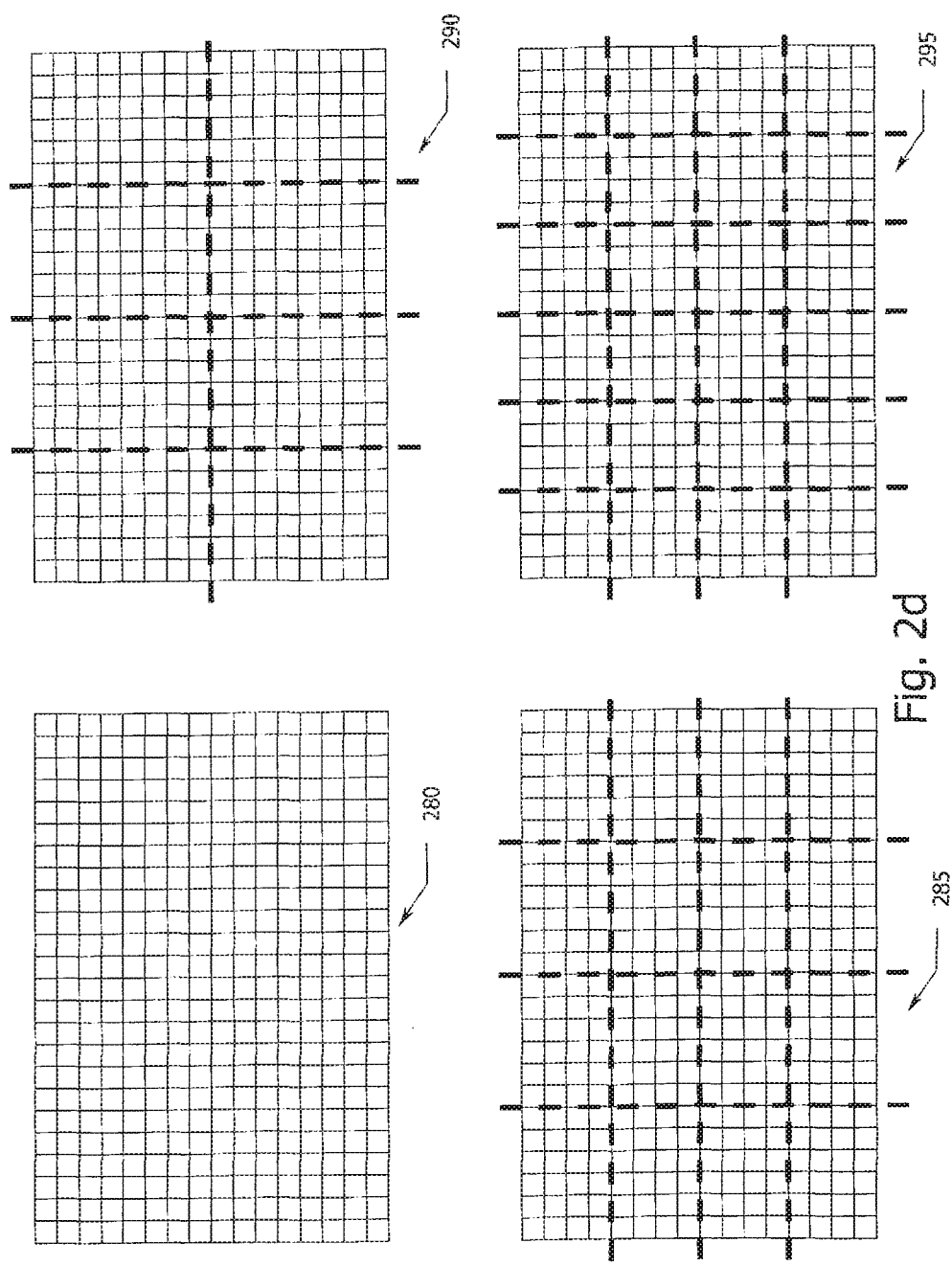
FIG. 2d illustrates four possible containment relationships for a 384-well plate.

FIG. 2c illustrates still yet other configuration variations that may be present in an assay plate; i.e., differing sector layouts, delineated by the heavy dashed lines 250, with identical well layouts, here a 96-well assay plate. FIG. 2d further illustrates representative sector layouts for a 384-well assay plate. FIG. 2e illustrates that in addition to having an assay plate 276 that could have non-uniform spot layouts from sector to sector 277, or even within a sector, an assay plate could also have non-uniform sector layouts 250.

As illustrated, it may be preferable to have many different types of assay plates. In addition to the differences existing in the number, arrangement, physical properties and shape of: wells, sectors, and/or spots. There could also be differences in the height of the assay plate, e.g., standard or deep-well, and in the shape of the well bottom (flat, round, conical, etc.). There may be some parameters associated, in particular, with ECL plates, e.g., the arrangement of electrodes, the distribution of electrodes into sectors, the nature of the electrodes (e.g., composition, surface treatment, etc.). The communication of the value of one or more plate-specific properties to an assay instrument may be crucial in the proper handling, processing or analysis of that plate by the instrument. Furthermore, certain instruments, e.g., ECL-based instruments, operate by stimulating certain regions of the plate through application of energy whereas others use fluidic control systems to move the sample out of a well and off of the plate to be assayed. These fluidics-based instruments must be capable of locating and lowering a probe/pipette into the well to aspirate the sample or to first mix reagents into the well and then aspirate the combined/mixed sample. Therefore, a given plate configuration, i.e., dimensions and well layout of the plate, would dictate the depth and motion profiles to be used by the system to operate the probe.

Figure 3:
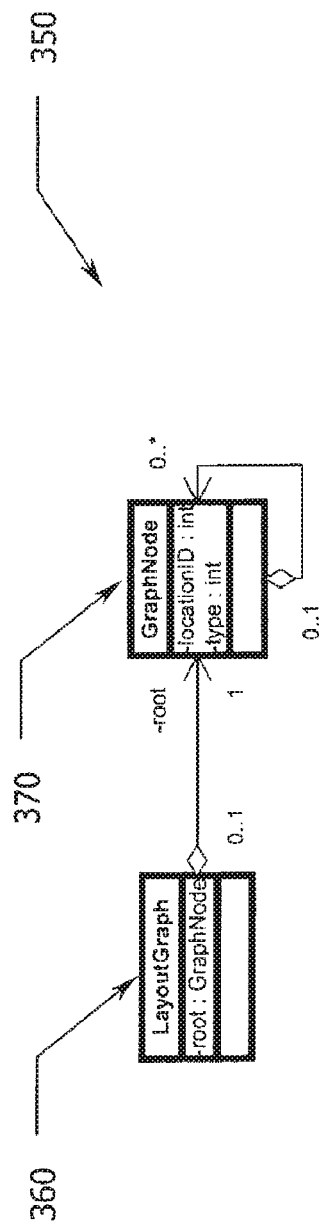
FIG. 3 is a UML representation of a tree data structure for defining different plate regions/locations.

FIG. 3 illustrates one preferred embodiment of the present invention that uses a design 350 that separates the definition of the plate region hierarchy from the association of data by using a graph data structure. One preferred embodiment of a graph data structure would be a tree data structure 350. Other preferred embodiments may also be used, where the graph data structure does not represent a tree data structure. A graph data structure is a collection of nodes and a collection of ordered pairs of nodes that represent links between the nodes. Links can be directed or undirected. A tree data structure is a graph data structure where all nodes have one parent except the root node that has no parent. In FIG. 3, a GraphNode class 370 represents a single region on the plate. The type attribute defines the kind of region. It can be one of any number of regions that may be defined on an assay plate. For example, if an assay plate is designed to have sectors, wells and/or spots, the type attribute could be one of the following values: {PLATE, SECTOR, WELL, SPOT}. Every node in the GraphNode class 370 is assigned a unique integer identifier, referred to hereinafter and in certain figures as a locationID. Each node in the GraphNode class 370 also contains a list of child nodes that represent its contained regions. Using the GraphNode class 370 to represent an assay plate would result in chains of nodes-containing-nodes and would form a tree structure of regions, where the root of the tree could be stored in a top-level LayoutGraph object 360. One example of such a tree structure is depicted in FIG. 4a.

For purposes of illustration, the tree structure 400 of FIG. 4a is created from the example plate 100 of FIG. 4b. Each node 405 on the tree preferably represents a specific, pre-defined location on plate 100 of FIG. 4a that is of a particular type of region; i.e., plate, sector, well or spot. As indicated above, a location, or region, of a plate is assigned a type value which enumerates whether it is a node with the type PLATE 410, a node with the type SECTOR 420, a node with the type WELL 430 or a node with the type SPOT 440. As can be seen from FIG. 4b, plate 100 contains two sectors, each sector contains two wells and each well contains two spots. Accordingly, with reference to FIGS. 4a and 4b the tree structure 400 represents the various regions of the plate 100: node 0 represents the plate 100 and has the type PLATE as indicated by the dashed box 410; nodes 1 and 2 represent the sectors 110 contained by plate 100 and are of the type SECTOR as indicated by the dashed box 420; nodes 3-4 and nodes 5-6 represent the wells 120 contained by sectors 110 and are of the type WELLS as indicated by the dashed box 430 (nodes 3 and 4 are contained by the sector represented by node 1 and nodes 5 and 6 are contained by the sector represented by node 2); nodes 7-8, nodes 9-10, nodes 11-12 and nodes 13-14 represent spots 130 contained by wells 120 and are of the type SPOT as indicated by the dashed box 440 (nodes 7 and 8 are contained by the well represented by node 3, nodes 9 and 10 are contained by the well represented by node 4, nodes 11 and 12 are contained by the well represented by node 5 and nodes 13 and 14 are contained by the well represented by node 6).

Figure 4C:
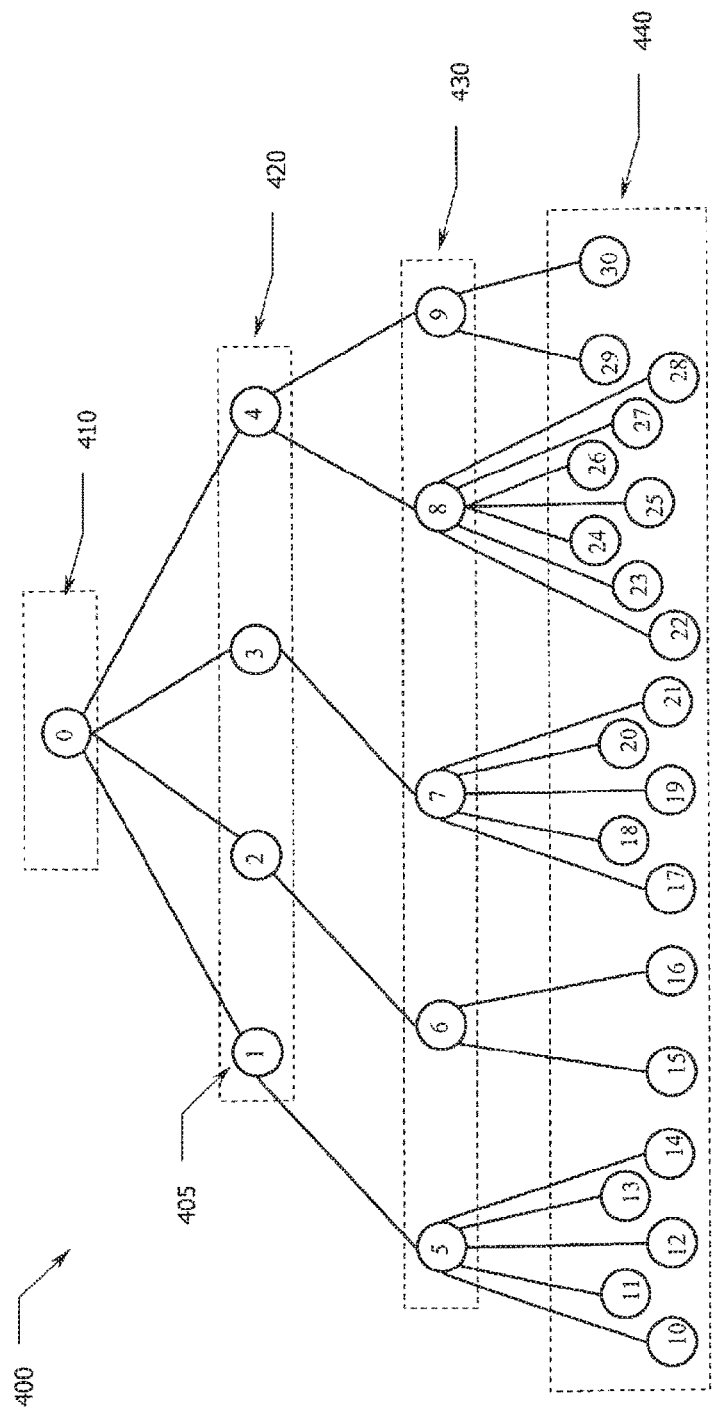
FIG. 4c illustrates a tree data structure representation of the plate in FIG. 4d that was constructed according to the UML representation of FIG. 3.
Figure 4D:
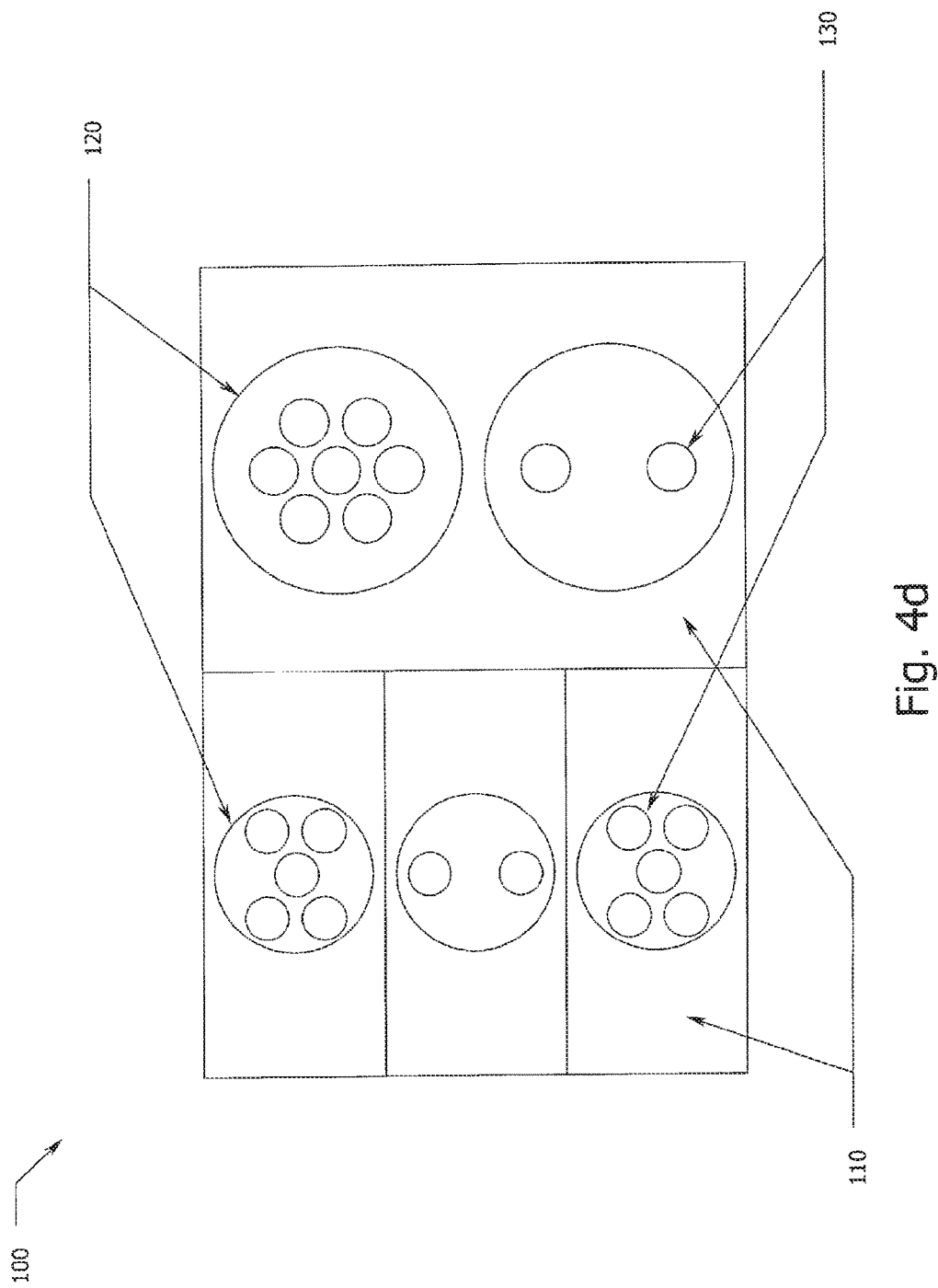
FIG. 4d illustrates an assay plate having a non-uniform sector, well and spot configuration as represented by the tree data structure of FIG. 4c.
Figure 4E:
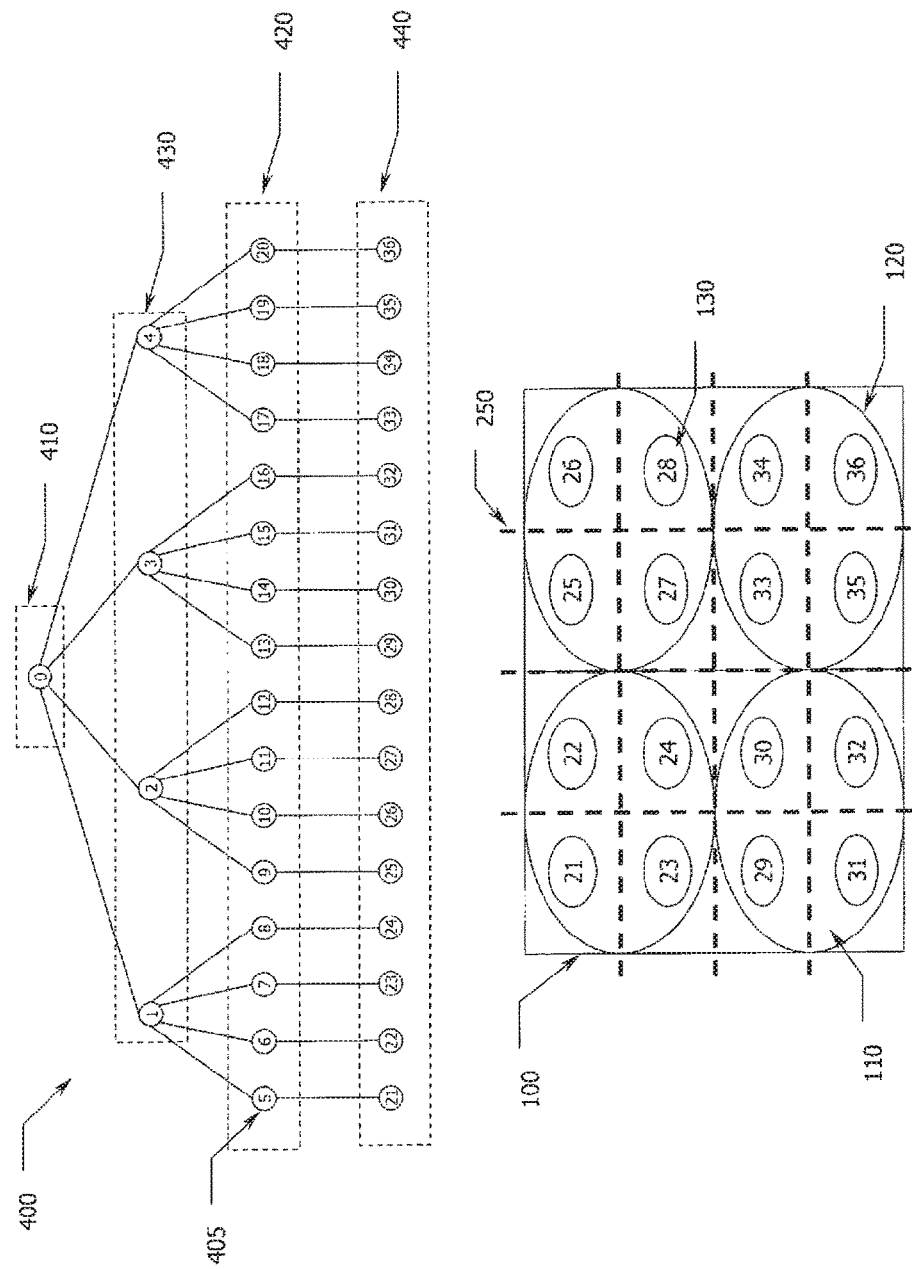
FIG. 4e illustrates a tree data structure representation of the plate in FIG. 1b that was constructed according to the UML representation of FIG. 3.
Figure 4F:
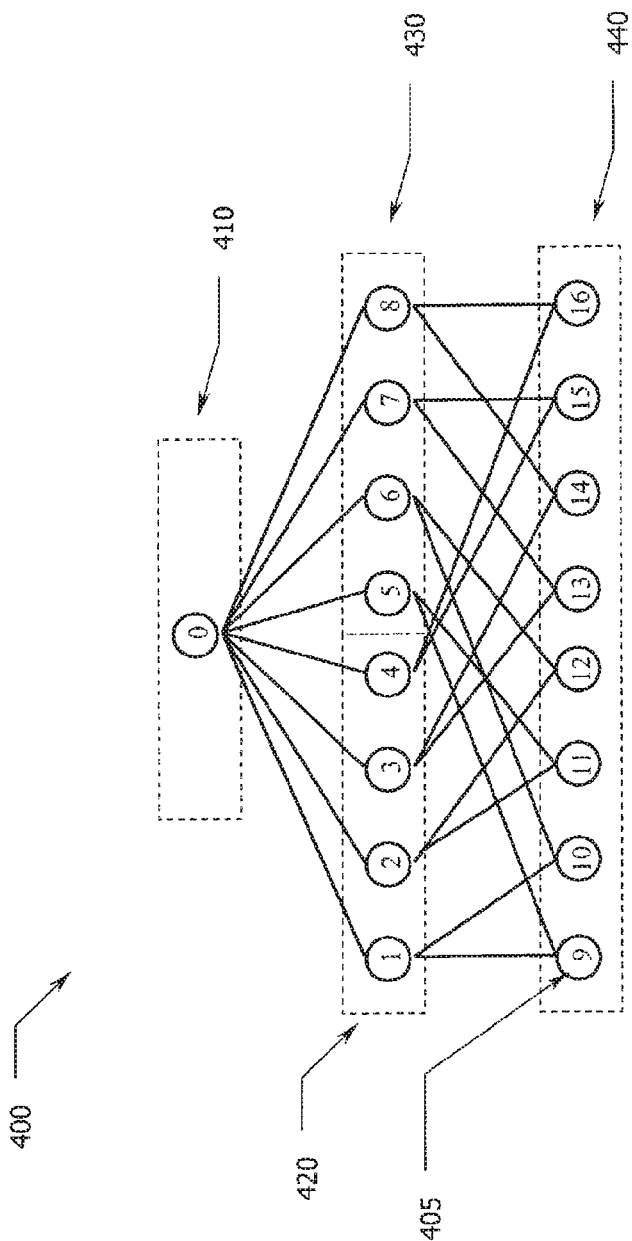
FIG. 4f illustrates a graph data structure representation of the plate in FIG. 1c having overlapping containment relationships.

It is important to note that the tree data structure representation of an assay plate is not limited to the example of FIGS. 4a and 4b. In particular, there is no requirement that sector layouts, well layouts and/or spot layout be uniform. FIGS. 4c and 4d illustrate a tree data structure 400 for an assay plate 100 having non-uniform sector 110, well 120 and spot 130 layouts. Additionally FIG. 4f illustrates a directed graph data structure 400, for an assay plate having spot 130 contained by both well 120 and sector 110, that would be represented by the more flexible directed graph. The node numbering, type enumeration and relationships follow the same hierarchy as that discussed in relation to FIGS. 4a and 4b and therefore will not be repeated.

Using such a tree data structure, data can be associated with regions of a plate by using a map of the unique integers, or location IDs, assigned to each node. As previously discussed, in certain preferred embodiments, a location (or region; these terms will be used interchangeably throughout) can represent the entire plate, a sector, a well, or a spot. Associating data with the plate is then a matter of mapping the location IDs to data objects that contain the data associated with a given location on the plate. This can be accomplished with a simple associative map data structure; e.g., an array, hash table, or the like. By using this tree data structure and this mapping/association scheme, the system can associate any data object with any region on the plate.

Data that may be associated with a plate or a predefined location on the plate include: a) detection parameters (temperature, applied waveform, camera settings for image capture (binning, sampling, etc.), exposure time of camera, volume of sample to be aspirated, type of sample to be aspirated and time to aspirate, mixing/agitation sample, cleaning cycle to be employed, and the like); b) read context (instrument configuration at time of read (e.g., information related to the specific camera, information related to the motion control system, information related to the ECL electronics/subsystem, and the like), temperature of instrument (e.g., temperature of CCD chip) at time of read, diagnostic data from instrument such as resultant waveform actually applied; c) raw assay test results (the actual test signal captured with a specific instrument prior to converting into, e.g., ECL count, image/signal statistics such as mean, standard deviation, and coefficient of variation, and the like); processed assay test results (e.g., conversion of raw signal into ECL count); interpreted assay test results (e.g., the ECL signal is mapped to a curve of concentration versus ECL to produce a concentration of the analyte in the sample).

In one preferred embodiment, the different data objects associated with a plate (e.g., detection parameters, read context, acquired signal, raw assay test results, processed assay test results, interpreted assay test results, and the like) can be organized into layer objects where each layer object provides a mapping of the data objects to the tree data structure; e.g., the location IDs are mapped, or associated, with appropriate data objects. For example, in the context of an ECL-based assay, one layer may contain ECL result objects, or detection signal objects, while another may contain detection parameter objects. A plate may contain any number of layers that each represent a particular type of data and each can be identified by a name that can subsequently be referenced.

Separating the structure of a plate (e.g., the location ID graphs of FIGS. 4a and 4c) from its associated data (layers of data objects), in accordance with a preferred embodiment of the present invention, confers a number of advantages over the prior art. In particular, it is very flexible for representing and processing many different plate configurations. This is possible since a single node object represents each location, and the graph of nodes can represent any containment relationship; i.e., locations of type SECTOR can be contained by nodes of type WELL, or vice-versa. Additionally, plates that do not contain sectors or spots can be represented in the tree structure as such, with the location ID graphs having only plate and well nodes.

Another advantage is that a data structure in accordance with the present invention allows a plate structure to be re-used in memory and therefore is very memory efficient. For example, when performing high throughput screening and multiple plates of the same type are processed, the plates can share a reference to the common graph and the plate structure need only be represented once, instead of once for each plate. A still further advantage of a preferred embodiment implementing a data structure in accordance with the present invention is that memory is conserved when representing and processing sparsely populated assay plates since the size of the data object mapping is preferably variable inside each layer object. Therefore, partially populated plates require less memory storage space.

Still further, in a particularly preferred embodiment, any data object can be associated with any plate location since the layer object preferably maps/associates location IDs to the data in a generic way. For example, some instruments may require that detection parameter objects be associated with sectors whereas other instruments may require that they be associated with wells. Even further still, new types of data objects could preferably be added to the system without requiring modifications or re-compilation of the plate source code, as would be required in a design that did not separate the plate structure from its associated data. This is possible since in preferred embodiments the layer class can hold objects of any type. Therefore if, in a particularly preferred embodiment, a new instrument is developed that requires a new data object, an existing framework constructed in accordance the present invention will support use of the new objects.

Instruments of the present invention, preferably, represent the plate structure flexibly so as to provide the ability to deploy new plates after an instrument has initially been fielded. Field deployed plates could have many different configurations, different overall designs or design features, different handling and/or processing requirements, and the like. For example, instruments, such as ECL-based instruments, that detect luminescence via an optical detector (e.g., CCD camera, photodiode, photomultiplier tube, or the like) could require conditioning and/or processing of the optical detector's detection signal (e.g., the detection signal might be converted into an associated test result). New plate types for ECL-based instruments could require that different signal processing/conversion algorithms be applied to the acquired detection signal in order to convert it into a valid test result. Still further, improved processing/conversion algorithms could be discovered and applied to preexisting data in order to produce a corrected test result; e.g., CCD chip defect correction, background image subtraction/correction, cosmic ray removal/correction, hardware binning, software binning, image transposition, creating and applying a well mask to locate the wells and/or spots, image alignment/centering, averaging, cross-talk correction, dark image detection, saturation detection and other factors which may affect image acquisition/analysis, and the like.

Instruments according to particularly preferred embodiments of the invention could conveniently use an integrated bar code reader, or other machine vision device, to read bar codes, or other machine-readable indicia, incorporated onto the plate; new plate types could require different bar code parsing algorithms. Therefore, systems and methods according to the present invention support not only the field deployment of new plate types represented by static data (e.g., physical dimensions, sector, well, spot layouts, etc.), but also new plate types requiring new processing algorithms such as, e.g., signal conversion, data analysis, data visualization, and the like. Preferred embodiments make use of a software architecture for plate representation that supports upgrade modules containing both static data and algorithms. In further preferred embodiments, an integrated bar code reader could allow an instrument to automatically identify the plate type currently being processed by the instrument, retrieve the appropriate information associated with the plate type and appropriately configure itself to process the plate. In addition, an integrated bar code reader could preferably allow an instrument to recognize a new or unknown plate type and proceed accordingly. Furthermore, optional information could be encoded in a bar code, or other machine-readable indicia including, but not limited to, information regarding reagents bound or otherwise stored on the plate (e.g., lot number, sequence number, calibration settings, and/or the like). For example, the bar code, or other machine-readable indicia, could be read from a plate when the plate is loaded and parsed by the instrument's host computer system in accordance with the appropriate parsing algorithm to retrieve the corresponding information and associate it with the plate.

Still further, certain instruments produce data in addition to the test results, e.g., ancillary data, that preferably is associated with particular plates or even particular locations on a particular plate. Additionally, different plate types and different instruments could require that certain types of data be associated with particular locations on a particular plate as well. Systems and methods using a flexible data representation of the plate, according to preferred embodiments of the invention, account for the ancillary data requirements of different plate types and different instruments, as well as future plate types and future instruments. For example, systems and methods according to the present invention preferably accommodate data associations including, but not limited to: a) assay signals (e.g., the amount of emitted light in the case of an ECL-based instrument) could either be associated with a particular well or with a particular spot within a well; b) the temperature of the instrument at the time the plate is being processed may be associated with the entire plate, a sector, or a well, or any combination thereof (this flexibility is particularly useful in assay formats, e.g., ECL-based assays, that are temperature sensitive); c) the parameters used to acquire a particular detection signal, i.e., the detection parameters, could be associated with the entire plate, a sector, a well or a spot, or any combination thereof; d) the configuration of the instrument at the time the plate is being processed might be associated with the entire plate, a sector, or a well, or any combination thereof; e) information relating to the test sample and/or assay reagents may be associated with the entire plate, a sector, a well or a spot, or any combination thereof; f) information related to instrument calibration or validation (e.g., the electrical current measured during an ECL measurement, the radiance of a light source used for a fluorescence, absorbance or light scattering measurement, and the like) could be associated with the entire plate, a sector, a well or a spot, or any combination thereof; and g) atmospheric pressure, date and time at which a measurement or manipulation was carried out, name of operator, and the like, could be associated with the entire plate, a sector, a well or a spot, or any combination thereof.

Finally, the plate data representation may be used for a number of different tasks including, but not limited to: collecting and storing test results; associating ancillary data such as detection parameters, temperature, and instrument configuration with the test results; defining the location coordinates of the wells that a probe should visit; and rendering the plate and its contents in a graphical user interface.

Figure 5:
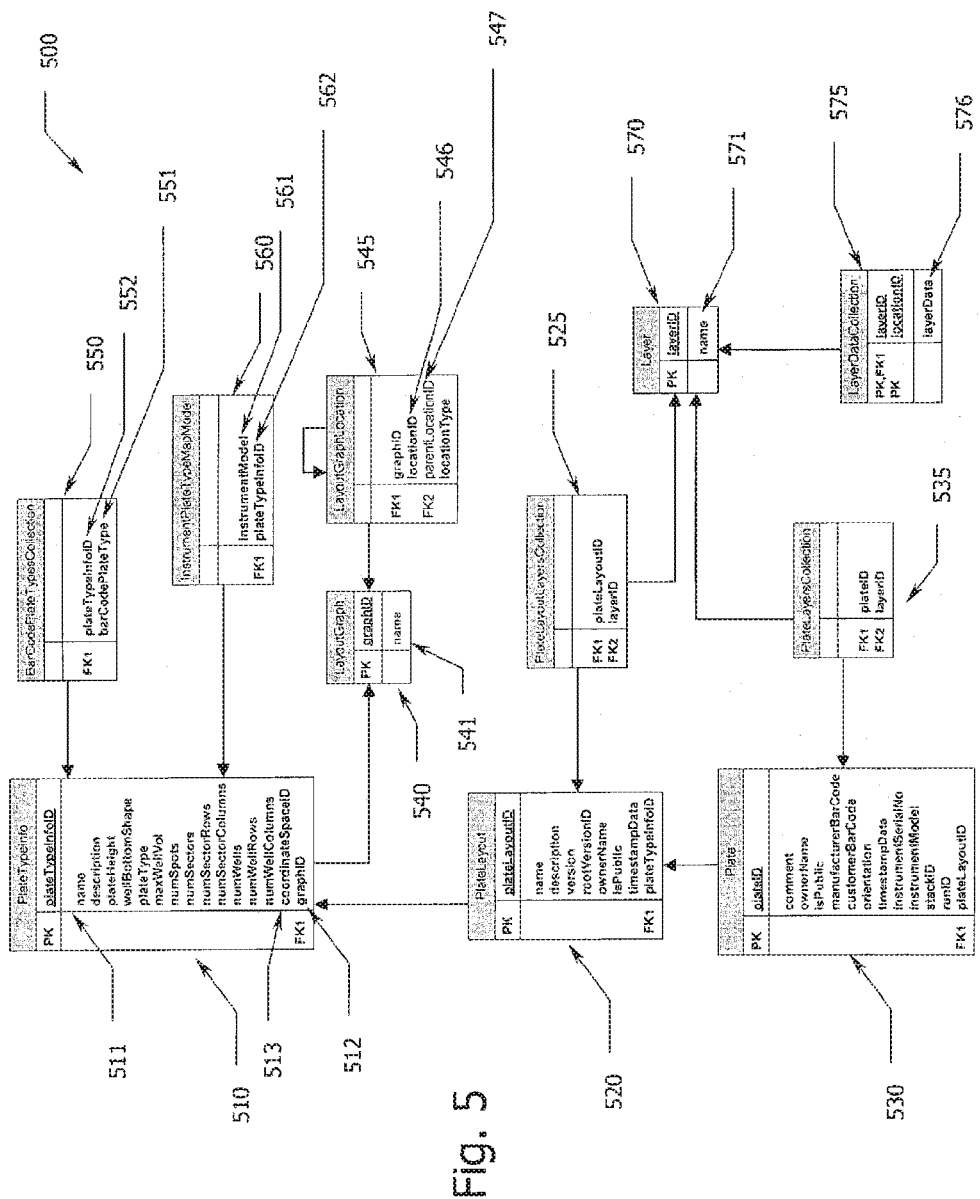
FIG. 5 depicts a representative Entity-Relationship (E-R) diagram utilizing a tree data structure representation of an assay plate.
Figure 6:
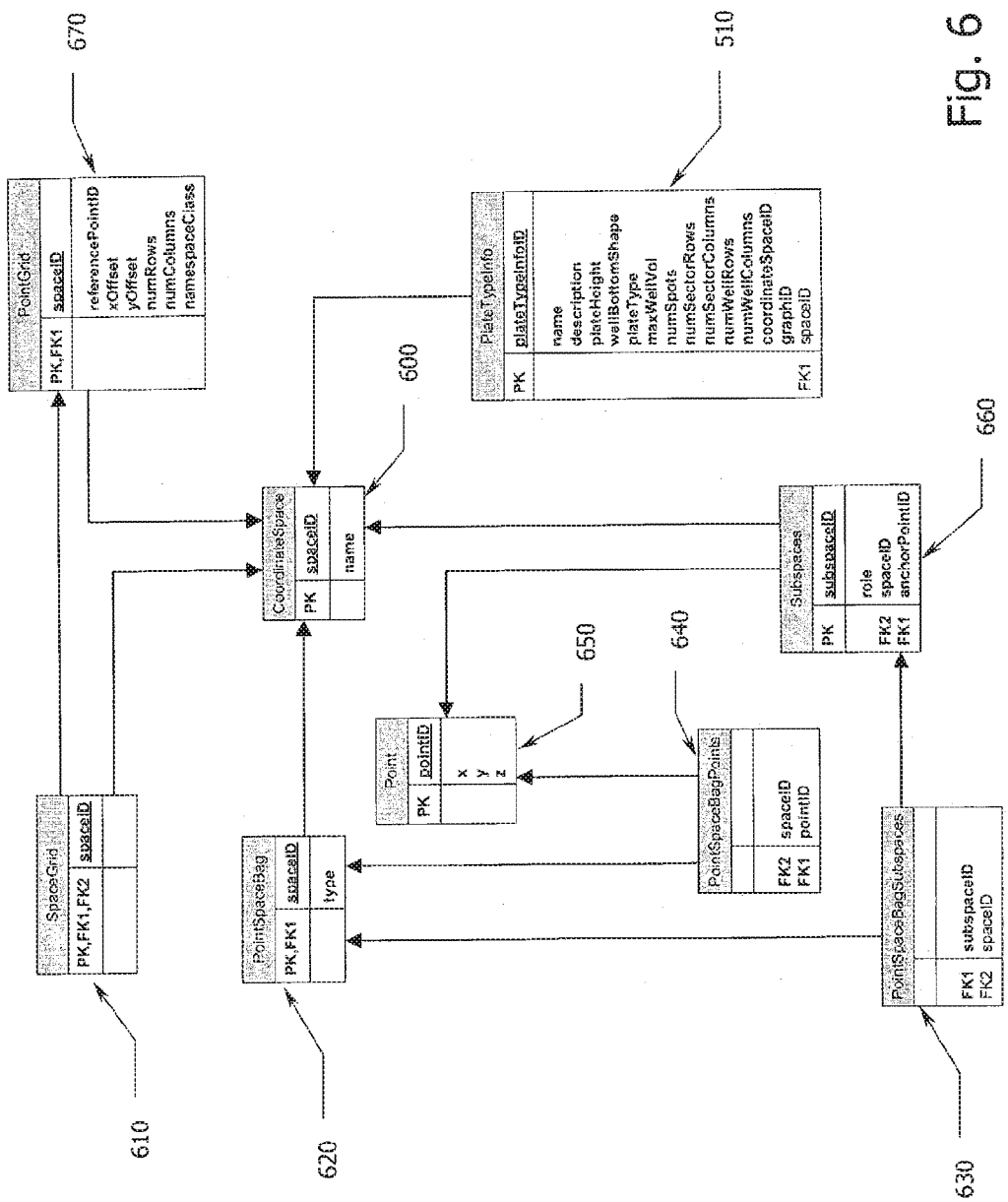
FIG. 6 depicts the geometry information associated with a given assay plate of FIG. 5 in representative E-R diagram format.
Figure 7:
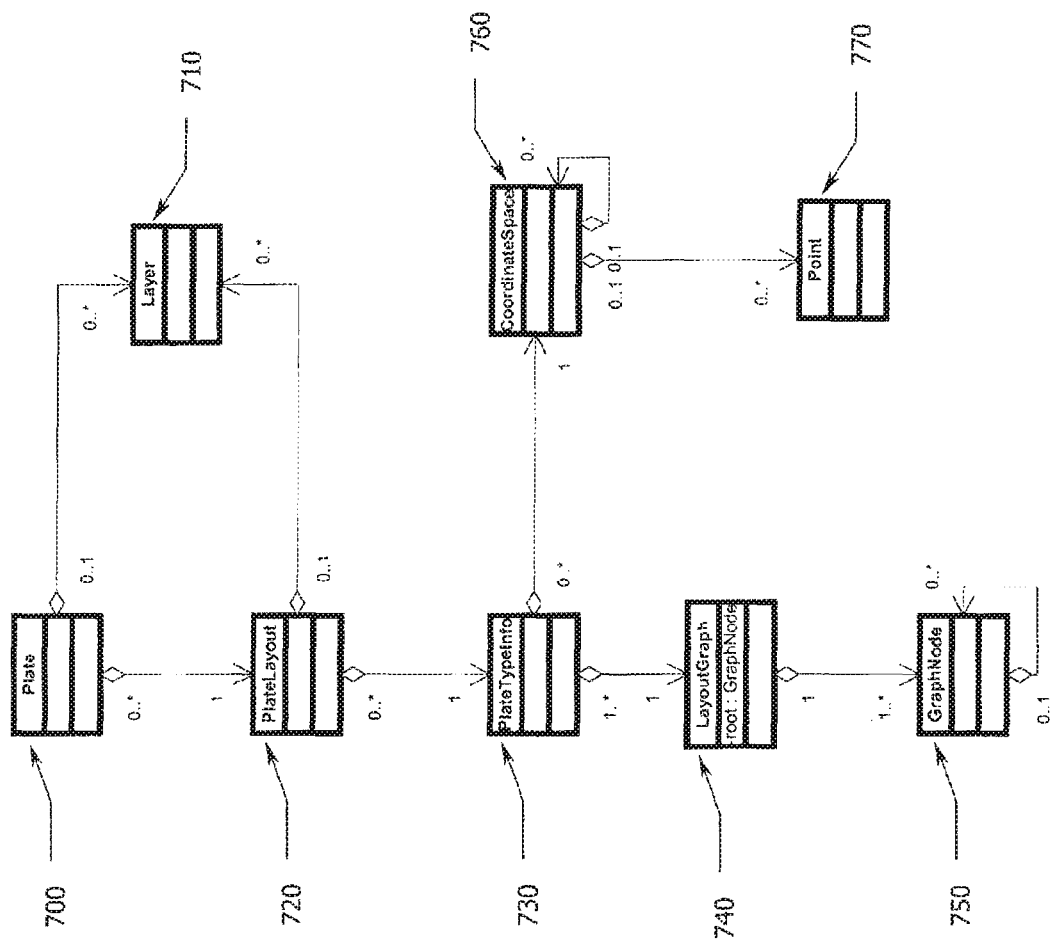
FIG. 7 depicts a representative UML class diagram for an architecture utilizing a tree data structure representation of an assay plate.

FIGS. 5, 6 and 7 illustrate a preferred embodiment implementing a tree data structure approach in accordance with the present invention. FIG. 7 is a Unified Modeling Language (UML) representation of one possible software architecture, i.e., a class diagram, that can be used to flexibly represent an assay plate and its associated data in accordance with the present invention. The architecture depicted in FIG. 7 consists of a top-level Plate class 700 which contains a pointer, or reference, to a PlateLayout class 720 that can reference PlateLayout objects for associating locations on the plate with numeric Location IDs (as indicated previously, Location IDs can be unique integers assigned to each node representing a predefined location on an assay plate). The PlateLayout class 720 contains a pointer, or reference, to a PlateTypeInfo class 730 that can contain data related to the plate including, but not limited to, a plate type ID, name, number of wells, number of sectors, number of spots, and well shape as illustrated in the E-R diagram of FIG. 5 by the PlateTypeInfo entity 510. The PlateTypeInfo class 730 contains pointers, or references, to both a LayoutGraph class 740 and a CoordinateSpace class 760. The LayoutGraph class 740 instantiates objects that define the locations on the plate and location ID hierarchy of sectors, wells, and spots through the GraphNode class 750 (discussed above in relation to FIG. 3). The CoordinateSpace class 760 instantiates a tree of CoordinateSpace objects that provide detailed geometrical information about the dimensions of the plate and the wells including the specification of predefined points instantiated by the Point class 770 (discussed in greater detail below). The Plate 700 and PlateLayout 720 classes both contain references, or pointers, to the Layer class 710. The Layer class 710 instantiates objects that associate data objects (e.g., configuration items, detection parameters, read context, acquired signal, raw assay test results, processed assay test results, interpreted assay test results, and the like) with one or more Location IDs.

As indicated in FIG. 7, the CoordinateSpace class 760 contains a number of other instances of CoordinateSpace that represent its subspaces 760; e.g., FIG. 6. In this manner, the CoordinateSpace 760 is a tree of objects representing the plate geometry. In certain preferred embodiments a the invention, automated fluidic-based instruments (e.g., dispensers, plate washers, fluidic-based analyzers) are used to introduce and/or remove samples and/or reagents from an assay plate. In one example, a automated fluidic-based analyzer performs assays by positioning a probe at appropriate locations within various wells of an assay plate, aspirating samples from the assay plate and transferring the samples into a vessel or chamber for testing. These instruments require detailed geometrical information (e.g., detailed geometric descriptions of the assay plates). For instance, a fluidic-based instrument utilizing one or more probes, or pipettes, would typically have to move the probes precisely over one or more wells and may also have to precisely position the probes to a certain depth/position within the wells. Such an instrument would typically have to calculate the relative position of the probe and/or probe tip with respect to the assay plate and each of the wells. For typical instruments, this information would be used to compute the number of motor steps that would be required to move the probe to the appropriate locations within various wells of the assay plate.

Since each plate type may be usable in multiple instruments, a flexible data structure for representing an assay plate would be advantageous. Variations across instrument motor configurations, such as, e.g., instruments that use different motors (different motors could have different performance and/or tolerance characteristics) and/or number and arrangement of motors, would result in variations in how an instrument positions a probe to aspirate the contents of a well. It would be very inefficient to try to store multiple collections of motor steps for each plate-instrument combination and each plate-instrument motor configuration. Moreover, newly introduced instruments that use a preexisting plate type would greatly benefit from a flexible data structure as well.

Figure 8:
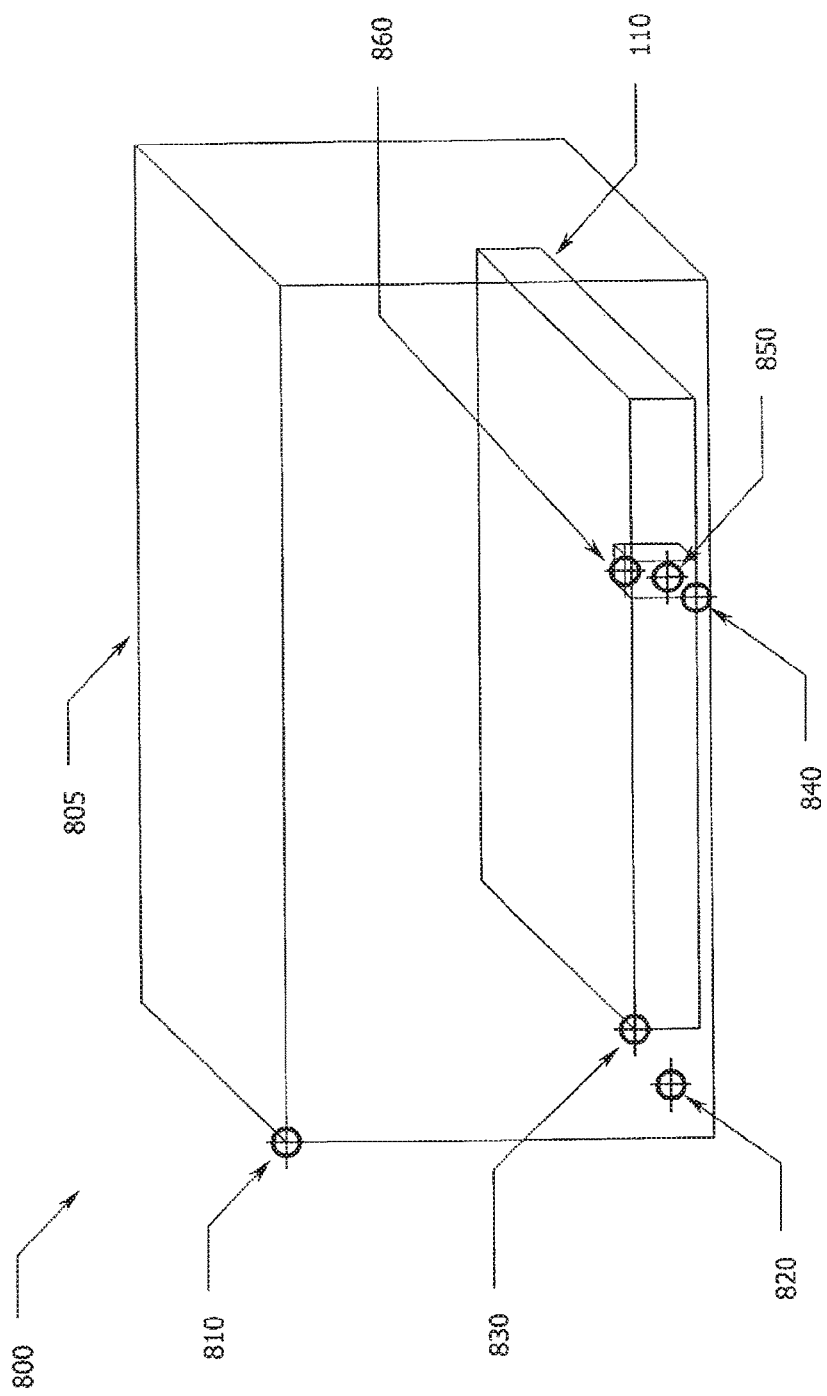
FIG. 8 is a simplified depiction of an instrument system having a global coordinate system and various local coordinate system anchor points.
Figure 9:
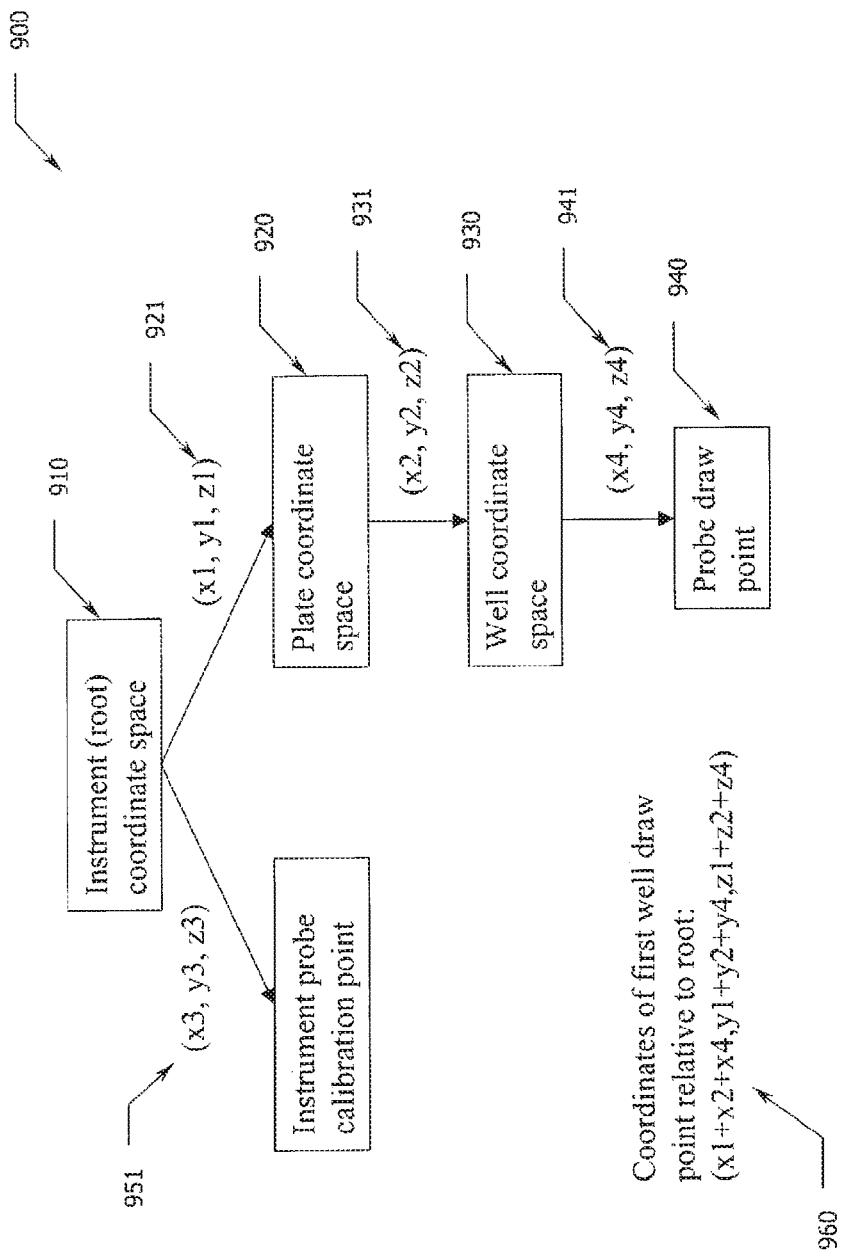
FIG. 9 depicts the hierarchy of the local coordinate systems to the global coordinate system.

FIGS. 8 and 9 illustrate one embodiment wherein the geometry of the system could be modeled/represented using a tree of nested coordinate spaces 900. Each coordinate space could be a collection of points and a collection of subspaces. The points could be represented as x, y, and z for three-dimensional Cartesian spaces, or as r, theta, and z for cylindrical spaces. Child subspaces of a space could simply be coordinate spaces that are anchored in their parent space by an anchor point 921, 931, 941; e.g., the subspace's origin or other reference point. According to this embodiment, the nested coordinate spaces would form a tree structure 900 where each space models/represents the points and subspaces that it contains according to its coordinate system/space, without requiring any knowledge of its containing, or parent, space. A tree data structure representation of the plate would be modular and reusable.

A preferred embodiment could model points using a consistent and convenient unit of measure, e.g., millimeters, and the instrument could be configured with a ratio of motor steps per unit. The tree coordinate space representation of such an embodiment would be reusable across various instruments having different motor configurations as well as with newly introduced instruments. For example, an instrument could contain a root/global coordinate space/system 810 that could contain one or more reference points 820; e.g., an alignment point for a probe, or probe tip. In a preferred embodiment, a plate type could be associated with geometry information that includes a coordinate space for the plate 830; i.e., a local plate coordinate space/system or plate space. This plate space could contain a number of subspaces 840 and points 850, 860. There could be one subspace associated with each well, a well subspace 840, and each well subspace 840 could contain one or more points 850, 860 defined within the well subspace 840; e.g., a well subspace could have at least one point that is directly above the well 860 and a point inside the well 850 from which the contents of the well could be aspirated. Moving the probe to a point of interest, either a desired location in the system or a predefined location on the plate (e.g., a well aspiration point 850), could be accomplished by traversing the tree of coordinate spaces.

In one embodiment, the system could be instructed to traverse the path from the point of interest to the root space by translating, or resolving, each point along the way into its parent coordinate space. Translating each point into its parent coordinate space along the entire path from the point of interest to the root coordinate space results in a globally resolved, or root translated, point 960 that is defined in the root coordinate space/system; i.e., the point of interest was initially a point defined in a local coordinate system and is translated, in a stepwise fashion, into the global, or root coordinate system. Moving the probe to the point of interest can then by accomplished by mapping the globally resolved point to motor steps required for implementing the move. In such a preferred embodiment, the instrument-specific software would only require a definition of the instruments global coordinate system 910, i.e., the coordinate space of the instrument, and the plate's local coordinate system's anchor point 921; i.e. the point at which the plate subspace is anchored to the instrument's coordinate space. The instrument could also be configured, preferably, with a motor "step ratio" for converting between canonical geometry units (e.g. millimeters) and instrument-specific units of motion such as motor steps. Therefore, a system implementing such a preferred method and architecture could process any recognizable plate type; e.g., when a particular plate type is loaded into an instrument, the system could identify the plate type, either automatically or through a user input, and retrieve the plate's coordinate space tree and nest it inside the root space at the plate's anchor point.

FIG. 6 illustrates one preferred embodiment of a database schema for implementing the methods described above. Preferably, the CoordinateSpace table 600 uniquely identifies and names every space. FIG. 6 illustrates three different relational representations of a coordinate space in accordance with one aspect of the present invention: the PointSpaceBag table 620; the PointGrid table 670; and the SpaceGrid table 610. The three relational designs represent different types of coordinate spaces in a space-efficient manner and, when loaded into memory as object instances, they all preferably implement the CoordinateSpace interface shown in 760. The PointSpaceBag table 620 has a collection of points 640 that preferably reference the Point table 650. It also has a collection of Subspaces 630 that are stored in the Subspaces table 660. Each subspace in turn references another record in the CoordinateSpace table 600 that is preferably one of the three types of spaces listed above. In a preferred embodiment, the PointGrid table 670 efficiently represents two-dimensional arrays of points; PointGrids have no child coordinate spaces but instead only have points. Rather than storing each point explicitly (e.g., as in the PointSpaceBag 620), the PointGrid table 670 preferably stores the number of rows and columns in the grid, the distances between rows and columns, and the coordinates of the point at grid location (0,0). Advantageously, this information is sufficient to generate the locations of all the points in the grid on-the-fly, or on an as needed basis. Preferred embodiments using this scheme are capable of representing arbitrarily large grids without the need for additional memory or disk resources. In a particularly preferred embodiment, the SpaceGrid table 610 is implemented as an extension of the PointGrid concept wherein a record in the SpaceGrid table 610 represents a grid of child coordinate spaces. The SpaceGrid table 610 uses a foreign key to the PointGrid table to store the same grid description information (number of rows and columns, etc.). Advantageously, instead of a single point at each grid location, the SpaceGrid 610 could contain a child subspace that in turn can be any one of the three types of spaces listed above.

One consequence of separating the plate structure from its contained data is that accessing the data can be counterintuitive. In certain preferred embodiments where the data is indexed by location ID, getting the data for a particular location on the plate could require interpreting the graph structure to find the desired location ID. In one embodiment, additional components could be used to simplify the task of interpreting and/or navigating/traversing the tree data structure by providing users with an intuitive method for accessing/referencing the data. Users and/or programmers are accustomed to addressing well locations on a plate by their coordinates (e.g., the top-left well on a plate is typically identified as "A1," where the letter denotes the row and the number denotes the column). For example, given a 96-well plate with eight rows and twelve columns of wells, users/programmers would normally prefer to identify the rows as A-H and the columns with the integers 1-12. Therefore, in one preferred embodiment, rather than users/programmers traversing trees and indexing plate locations by an opaque integer identifier, additional components commonly referred to as "helper classes" could preferably be employed. Helper classes, as that term is customarily understood in the art, are not persistent data objects that are stored in the database, but rather are classes of code that allow programmers re-use implementations of commonly needed logic. It is advantageous to have helper classes to interpret the tree data structure, or graph structure, without writing unnecessary tree traversal code; e.g., the helper classes could preferably provide an intuitive interface to the data while hiding the details of the tree structure from the user/programmer.

In one embodiment, two useful helper classes may consist of: a LayoutIndexer object that interprets the layout graph and provides mappings between grid rows and columns and the location IDs; and a LayoutIterator object that allows the software to enumerate a graph's location IDs by type.

Preferably, the iterator could be implemented/constructed such that it enumerates a collection of other objects. The iterator interface would preferably present a very simple interface to the user/programmer to enumerate, or identify, the next element in the collection while keeping the implementation details of the collection hidden. This would allow the user/programmer to focus on, or act on, the data in the collection rather than on navigating through the collection itself; e.g., to draw test data stored in a result layer on a grid in the user interface, a programmer would have to traverse the tree looking for locations that have result objects in the result layer.

Therefore, in order to retrieve data for a particular well without the aid of such helper classes, the user would first be required to find the location ID of the well. For example, if the user were interested in obtaining results for well C5 in a 96-well plate, the programmer would have to traverse the location ID graph, requiring knowledge of the number of rows and columns on the plate, as well as the numbering convention of location IDs, to find the location ID of the desired well. After determining the appropriate location ID for a particular location the user would then be able to retrieve the data from a layer associated with this location ID.

FIG. 5 depicts the Entity-Relationship (E-R) diagram illustrating a preferred embodiment for how plates (e.g., plate type information and data associated with each plate type and/or particular plates) are persisted, in the database. For purposes of illustration of the database schema of FIG. 5, the plates 100 of FIGS. 4b and 4e will be used to populate the database. The tables shown in FIGS. 5a-5k are based on these illustrative example plates of the configuration/layout shown in FIGS. 4b and 4e. The plates' layout graphs 400 are depicted in FIGS. 4a and 4e and sample, or "dummy," data is used here only to illustrate the plates' supporting/associated data. For this example, the plates' supporting/associated data will consist of detection parameters, test results and read context but can include any other data that needs to be associated with a plate or plate layout as previously discussed. Hypothetical sample data for five plates is illustrated in the tables of FIGS. 5a through 5k. As illustrated, three of the plates share a common layout; the remaining two plates have different layouts; and one of the plates has a different plate type with its associated layout graph shown in FIG. 4e.

Therefore in accordance with a preferred embodiment of the present invention, the supporting/associated data would be represented as three layers. Preferably, the DetectionParameter layer can be associated with a particular plate configuration/layout allowing it to be reused across many plates of the same configuration/layout, since the plates would share a common configuration/layout, and therefore a common structural representation; only the data associated with the running/processing of a particular plate on an instrument would differ from plate to plate. Since the data and structure are separated in a preferred architecture, the structural representation of the plate would preferably only be stored in memory once and data for numerous plates of this structural layout would, preferably, simply be mapped to the tree structure.

For the present example, it will be assumed that the plate layouts of FIGS. 4b and 4e require that their detection parameters be associated with each sector location 110. Further, it will be assumed that the plate layout requires the results to be associated with each spot location 130. Finally, it will also be assumed that the plate layout requires the read context data to be associated with the plate. In this example, the read context data is related to the state of the instrument at the time the plate is being processed/read. For example, as applied to an ECL measurement, read context data for the plate layouts of FIGS. 4b and 4e can include voltage and current information, temperature data, intermediate results, and the like.

In one preferred embodiment, each plate can be tracked by the system through a table including each recognized plate type; e.g., the PlateTypeInfo table 510 depicted in the E-R diagram of FIG. 5. Each plate type would preferably have a single record in this table containing some identifying information about the plate types and some basic physical characteristics of the plate including the rows and columns of wells and sectors, and the number of spots (see FIG. 5a). It could also preferably describe the shape and capacity of the wells. As illustrated in this example, each plate type 511 can be associated with a layout graph 512 and a coordinate space 513.

It should be noted that although the database schema of FIG. 5 depicts this table as containing fields for the number of rows and columns of sectors and wells, and therefore assumes that the sectors and wells possess a uniform layout, i.e., arranged in a grid, the schema need not necessarily make this assumption. The flexible data structure of the present invention is not limited to representing grids. A non-uniform sector, well and/or spot layout can be represented by the tree data structure in a straight forward manner since it preferably is only concerned with the structural hierarchy, or containment relationships, of the various plate locations. This is illustrated in FIGS. 4c and 4d, which depict plates having non-uniform sector, well and spot layouts.

As discussed above, in preferred embodiments, helper classes could be implemented to make the task of traversing the tree data structure, to ascertain the location ID of a particular node, simple. Therefore, simplified sector, well and spot layouts would merely represent particularly preferred embodiments that lend themselves to straightforward implementations of the helper classes; e.g., straightforward implementations of the LayoutIterator and the LayoutIndexer implementations.

Preferably, in order to greatly simplify and automate plate tracking, each plate type would have an associated bar code. Each plate type's bar code could be maintained in a table, e.g., the BarCodePlateTypesCollection table 550. This relational table could define the bar code identifiers 551 for each plate type 552. For plate types that preferably have bar codes, this table could contain the value that is encoded in the bar code to identify the plate type. Furthermore, as illustrated in FIG. 5b, each plate type could have any number of bar code identifiers.

In another preferred aspect, a table for tracking plate type compatibility with various instruments could provide a further enhanced tracking capability; e.g., the InstrumentPlateTypeMap table 560. Such a table could simply list the instrument model names 561 which can process each plate type 562. Systems and methods according to the present invention could preferably store this information FIG. 5c in memory or on an electronic storage medium and then use this compatibility data to determine whether a particular plate type is compatible with a specified instrument.

As discussed above, each new plate type would preferably have an associated layout graph that could be used to represent the tree data structure; e.g., LayoutGraph table 540. Each record in this table FIG. 5d could index the layout graph, preferably stored as a name 541, that describes the hierarchy of locations for a plate type. The layout graph would preferably be stored as a table; e.g., LayoutGraphLocation table 545. The LayoutGraphLocation table 545 would preferably contain the actual tree of nodes, e.g., locationIDs 546, and the parent node of each node, e.g., parentLocationID 547, that represent the predefined plate locations and the predefined plate location hierarchy for a given plate type. The table could take the form depicted in FIG. 5*e* wherein each record represents a location, with an ID, e.g., integer value, and a type. For embodiments using plate locations defined as plate, sector, well and spot, the type can be, e.g., one of {PLATE, SECTOR, WELL, SPOT}. It should be noted that the plate type could also be indicated by an integer, or any other alphanumeric character, or combination thereof, and do not necessarily have to be identified by their actual labels; actual, or descriptive, labels are used here for simplicity. Preferably, a foreign key to the table itself could identify the parent location, where, e.g., NULL indicates the root of the tree. In an alternative embodiment, the performance of the overall system could be enhanced by storing one or more layout graphs in a binary or text file; e.g., the Java programming language supports writing objects to disk as serialized objects.

To maximize reusability, in accordance with one aspect of the present invention, the flexible data architecture can be exploited by using a table containing data that may be associated with a particular plate layout; e.g., the PlateLayout table 520 (see also, FIG. 5*f*). This table contains PlateLayout objects, which are collections of the layered data objects, describing data associated with the plate; e.g., the PlateLayoutLayersCollection table 525 that lists the layers that are contained by, or associated with, a layout (see also, FIG. 5*g*).

As discussed above, certain data that is associated with a particular plate layout can be reused, e.g., indexed, by more than one plate of the same layout, or plate type. For example, a particular plate type may be designed such that one or more wells contain controls, calibrators, or the like. Since every plate of this layout would preferably have such controls, calibrators, or the like, in the same wells, or locations, the plate layout object could contain a reference to a sample layer object that marks/identifies the contents of each well. Additionally, in a preferred embodiment, the layout of a particular plate type could also reference a detection parameters layer object that contains data related to how the plate should be processed by an instrument. Therefore, plate types of the same plate layout could each reference the same detection parameters layer object; i.e., the detection parameters layer object could be reused (e.g., associated with) any number of plates. Advantageously, this would allow users to define an experiment once for use with many plates, where each plate shares the same format, as is the case, e.g., in high throughput screening.

Data that is unique to a particular plate can be stored, e.g., in a Plate table 530. In a preferred embodiment, the Plate table 530 could define individual plates (see, e.g., FIG. 5*h*), where each plate could be associated with a layout (see, e.g., FIG. 5*g*) and a collection of layer objects; e.g., the PlateLayersCollection table 535 that lists the layer objects that are associated with a plate (see also, FIG. 5*i*). The layer objects that are associated with a plate, as opposed to those contained in, or associated with, a particular plate layout, are preferably those that are specific to a particular plate. For example, the test results for a plate are stored in a layer in the plate. Alternatively, a detection parameter layer is associated with a layout, since layouts may be re-used across many plates. Additional information that can be included in the plate table according to a further embodiment might include, e.g., the owner (e.g., user that processed the plate), a field for user comments, bar codes, the serial number of the instrument, and the like (see FIG. 5*h*). In further preferred embodiments, other information that could also be included in the plate table could associate a plate with a stack of plates and/or a run of plates; i.e., a collection of stacks. For example, high throughput screening instruments that would preferably use plate stackers to load stacks of plates into an instrument for automated, successive/continuous processing could benefit from the ability to store and track information related to stacks or runs of plates.

The table in FIG. 5*k* illustrates the mapping of data objects onto the tree data structure. In the present example, the Layer table 570 depicts one preferred embodiment for mapping the nodes of the tree data structure, or the location IDs, to the associated data objects. As illustrated in FIG. 5*j*, each layer may be given a name, e.g., "detectionParameters" or "results" and can be associated with either the plates or the layouts (see FIGS. 5*g* and 5*i*).

Yet another aspect of a preferred embodiment uses a table to store the actual data in layer objects, e.g., the LayerDataCollection table 575, and preferably provides all of the data associated with a predefined plate location, e.g., the locationID. This table would preferably store the actual data in a layer wherein a record in this table represents a single data object associated with a specified location in the layout graph corresponding to a specified location on the plate (see, e.g., FIG. 5*k*). Additionally, this table may hold a reference to another layer object; e.g., as illustrated in FIG. 5*k*, a single test result or a reference to an object that contains detection parameters, may be stored for each locationID. For example, each entry in the table preferably associates a location ID to a data object (e.g., a result, detection parameter, read context, or the like). Throughout the description of preferred embodiments herein, no distinction has been made between "containing an object", "containing a pointer to an object" and "containing a reference to an object" and therefore the terms are used interchangeably throughout. It is noted that certain programming languages may require these distinctions to be made, however, this would not preclude systems and methods according to the present invention to be used with such programming languages. Finally, it should also be noted that, for the sake of simplicity, and for purposes of illustration, the LayerDataCollection table 575 contains a foreign key reference to a generic collection of data object tables that are not depicted in FIG. 5.

In accordance with one aspect of the present invention, using a tree data structure to flexibly represent and process an assay plate supports the deployment of new plate types after an instrument has already been fielded; i.e., installed at a user's site. In one embodiment, a plate types directory can be maintained in memory, stored in either a local or remote database, on an electronic storage medium, or the like, that is accessible to the instrument software. Preferably, this plate types directory could contain plate deployment files representing one or more of the plate types that an instrument is capable of supporting. These plate deployment files could contain static data used to describe the plate types (e.g., the name, description, plate type ID, geometry, location. ID map, and the like) and/or algorithms (e.g., signal conversion, data analysis, data visualization, bar code parsing, and the like). In addition, these files could also contain software/program code required by a specific plate type (e.g., code for rendering, analysis, data visualization, and the like). Optionally, these files could also contain software/program code useful for populating the system's database (e.g., on the instrument's host computer, on a remote computer, on a server, and the like) with the appropriate plate data. For example, the plate deployment files could contain code for populating a database such as the preferred database schema depicted in FIG. 5.

In one embodiment, the field deployment of new plate types could be accomplished by adding a new plate deployment file to the plate types directory, either on a computer readable storage medium or directly into memory. In a preferred embodiment, a "JAR file" could be utilized to store the necessary static data, algorithms and/or software/program code that could be required to deploy a new plate type; a "JAR file" is a type of file that archives Java code and other data. In one embodiment, the JAR files could contain a registry of plate type information in the form of a property file in the JAR file. One or more entries in the property file would preferably map string keys to string values. Furthermore, in certain preferred embodiments, the property file could be used to define the unique plate type ID for the JAR file and a number of resource entries. Alternatively, the instrument system's software could automatically assign a unique identifier for the plate type. In particularly preferred embodiments, some of the entries could represent algorithms or the name of a Java class implementing the algorithm. For example, one embodiment might use a JAR file created for a particular assay plate, which was designed to be used by an instrument that requires image processing algorithms, containing an entry for a saturation detection algorithm.

In a preferred embodiment, the JAR file could contain Java code, serialized Java objects, configuration files, icons, and the like, each appropriately indexed by a property file or manifest file; e.g., JAR files include a manifest file stored in each JAR file or a separate file could be included within the JAR file. An example of a preferred property file with illustrative entries is given in FIG. 5*m*. As seen in the example resource property file, both algorithms and static data can be included in the corresponding JAR file. In a preferred embodiment, a PlateTypeID attribute could be used to define the unique identifier for the plate type. Additionally, the example property file also illustrates the reference to several image processing algorithms. Preferably, the image processing algorithms could be referenced by specifying the Java classes that implements them (as can be seen from FIG. 5*m*, a single class, HTS96W1SimageProcessor, can implement one or more algorithms). Further illustrated by the example property file is the ability to store, or archive in the plate deployment file, the location ID graph for the plate in the form of a serialized object file, indicated by "type5graph.ser."

Alternative embodiments might use a mechanism besides JAR files to deploy modules of executable code. These mechanisms may include Dynamically Linked Libraries (DLLs), Unix-style shared objects, interpreted scripts (such as Perl, Python, and the like) or any other means of deploying code.

Figure 10:
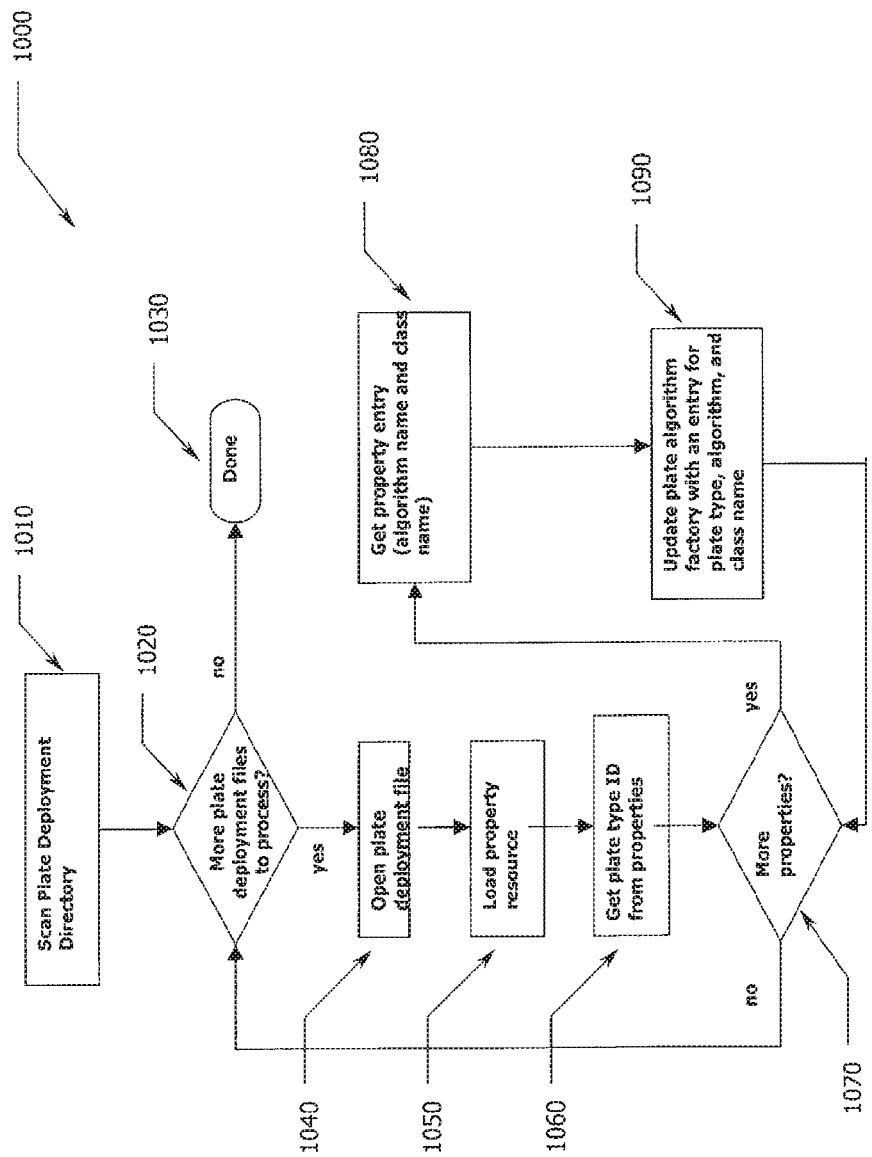
FIG. 10 is a flow diagram illustrating one possible process for deploying new assay plate types using plate deployment files defining the new assay plate.

Turning now to FIG. 10, a block diagram illustrating an example of one preferred embodiment for a method of deploying new plate types is depicted. In one preferred embodiment, the plate type, or plate deployment, directory (the terms plate type directory and plate deployment directory will be used interchangeably throughout) could be scanned 1010 (e.g., either when the instrument software is first started or when so directed by a user input) and a determination would be made whether there are plate deployment files to be processed 1020. If it is determined that there are plate deployment files to be processed, an instruction would be issued to access the plate deployment file 1040. The contents of the plate deployment file would then, preferably, be parsed by the software running on the instrument's host computer, or on a remotely connected computer, and one or more property resources would be loaded 1050 and the plate type ID property ascertained/determined 1060. At step 1070, the system could then ascertain/determine whether any additional properties are available for processing 1070. If there are additional properties, the system could then retrieve the property entry 1080 and preferably add the appropriate table entry into the database 1090. Steps 1070 through 1090 would then preferably be repeated until there are no additional properties from the plate deployment file being processed. At step 1020 the system would determine whether additional plate deployment files are available for processing. If there are additional plate deployment files, the system could then, preferably, repeat steps 1020 through 1090 until all plate deployment files have been processed 1030.

Figure 11:
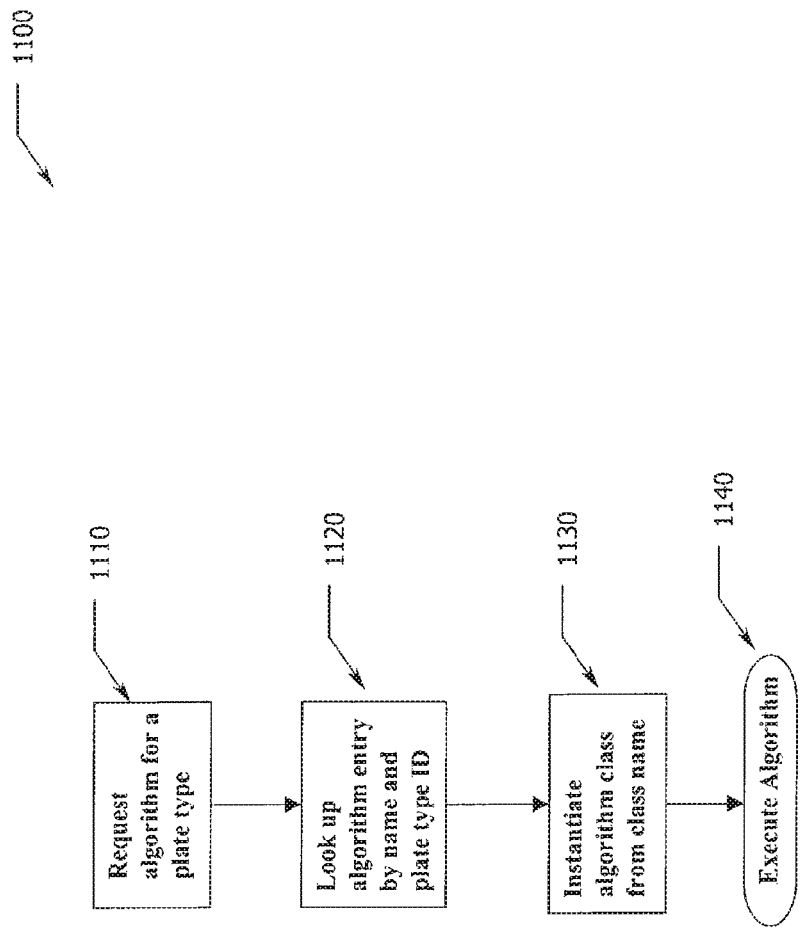
FIG. 11 is a flow diagram illustrating one possible branch process for processing a new assay plate type requiring new processing algorithms.

As depicted in FIG. 11, a still further embodiment might include a method by which the instrument's host computer system, or remotely connected computer, could read the property files in each plate deployment file and preferably use them to build a factory object that can instantiate instances algorithm objects. A factory is a commonly known object-oriented design pattern known to those proficient in the Art, that uses one object to instantiate other objects. The algorithms instantiated by the factory may preferably include, but not be limited to, bar code parsers, image processors, rendering algorithms, or the like. Thereafter, at a point when the system requires an algorithm for a specific plate type, it could preferably request from the plate algorithm factory the algorithm appropriate for the specific plate type 1120, e.g., using the appropriate name. The factory would then preferably look up the plate deployment file and class name associated with the algorithm 1120 and create an instance of the class 1130. The system would then preferably call methods on the algorithm instance to begin its execution 1140.

Recognizing that many algorithms may potentially be re-used across different plate types, the system could preferably maintain a default list of algorithms that resides outside of any specific plate deployment file; e.g., in static memory, dynamic memory, on a machine-readable storage medium, or the like. For example, with reference to FIGS. 11 and 5*m*, when the system requires a particular algorithm (e.g., an algorithm to draw/paint the spots in a well on the screen) it would preferably look up the value for the "SpotRenderer" key in the property file for the plate type being drawn. The value of that key is the name of a class file contained in the plate deployment file that implements the algorithm. The system would then, preferably, load the class from the plate deployment file, create an instance of the class and then call a method on the object to do the rendering.

Figure 12:
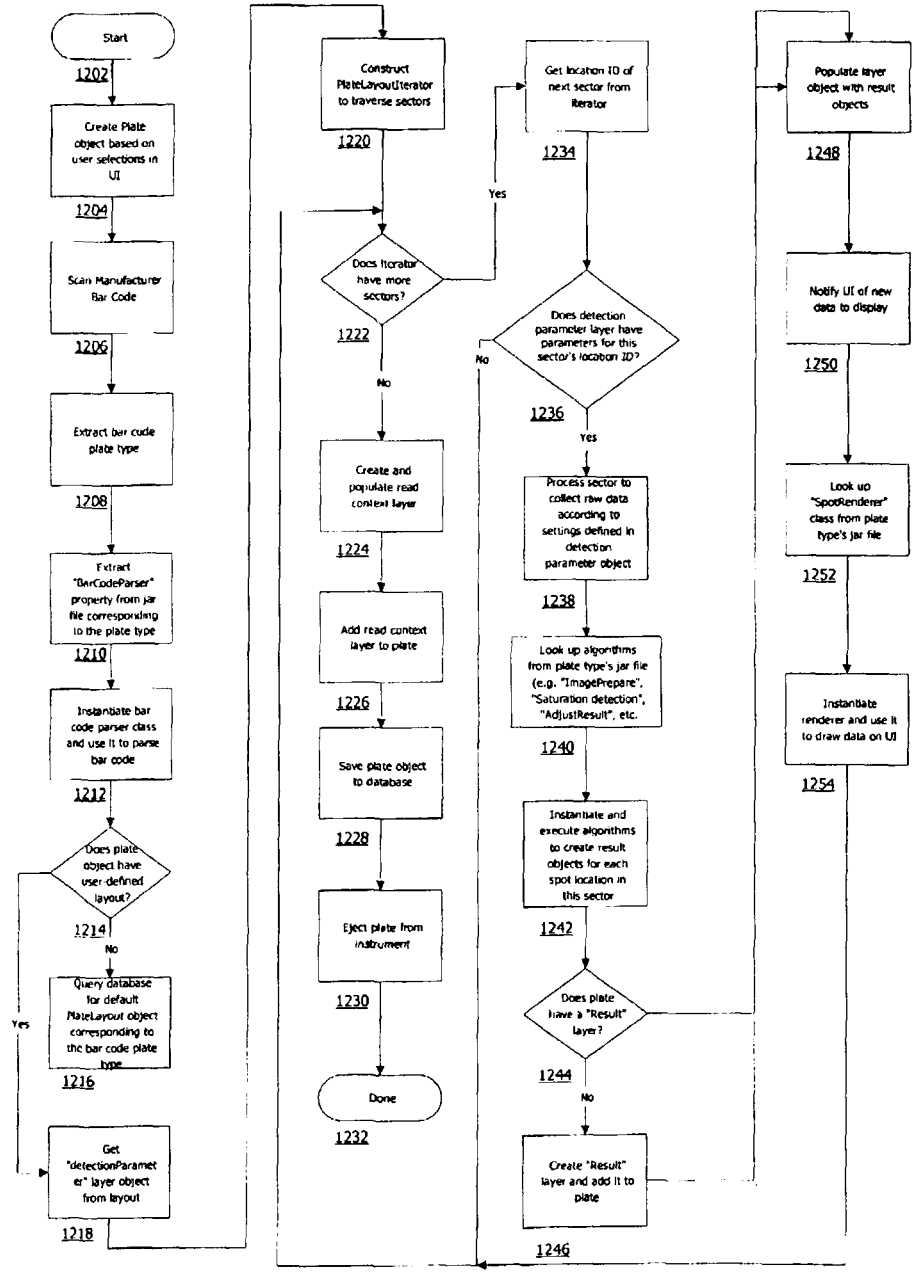
FIG. 12 is a flow diagram illustrating the overall operational flow of preferred systems and methods according to the present invention.

An overview of a preferred method of operation for instrument systems according to the present invention will now be described with reference to FIG. 12. An example of a preferred system and method for reading an assay plate. The process preferably begins with a user interacting with the instruments host computer system's software application through a Graphical User Interface (GUI). In one embodiment, a user could initiate the plate processing procedure, or the plate run process (either manually or through automated means), load the plate onto the instrument (either manually or through automated means) and specify any necessary configuration settings. The system would then preferably create a plate object for the run 1204. In a preferred embodiment, the instrument would then read the manufacturer bar code 1206. The system at step 1208 would then perform a database look-up to determine the plate type identifier associated with the scanned bar code from step 1206. After identifying the plate type, the system would preferably use the methods of FIG. 10 to find a bar code parser algorithm capable of parsing the bar code 1210. The parser could extract items such as the lot number of the plate, the date of manufacture, the expiration date of the plate, and the like 1212. The system would then store this data in a plate object.

The system could then check the input plate object to determine if it contains a layout object specified by the user 1214. If no user specified layout object is found, the system could then load a default layout defined/associated with the plate type 1216. The instrument would then preferably extract the detection parameter layer from the layout 1218. Using a helper class 1220, 1234, e.g., a PlateLayoutIterator object, the system could enumerate the location IDs of the sectors on the plate. All sector location IDs for which the detection parameter layer contains parameters are then preferably read by the instrument 1238. During this processing, the instrument software may need to run any number of algorithms specific to the plate type to perform the read 1240, 1242. These algorithms are preferably executed according to the procedure shown in the preferred embodiment of FIG. 10. As each sector is processed, the system would preferably create Result objects for every location where a read occurs. For example, on instruments that support bound chemistry on the plate, a Result could be created for each spot; other instruments may create a single result for each well. A layer object is created to hold these results 1246 and the result objects are added to the layer and associated with their respective location IDs 1248.

After each sector is processed and its result data is added to the layer, the GUI is notified to update the display 1250. Using a PlateLayoutIterator object, the GUI could traverse the locations that are descendents, or part of the hierarchy, of the sector location ID. The GUI could then obtain a rendering algorithm for each well using the process depicted in FIG. 10, and use the algorithm to draw the data on the screen 1254.

Once all the sectors have been read, the system creates and populates the read context layer 1224, and adds it to the plate 1226. The plate object and one or more of its associated objects are then stored to the database 1228; preferably all of the associated objects are stored to the database. At this point the instrument is finished with the read, and the plate is ejected 1230.

A computer system for implementing methods in accordance with preferred aspects of the present invention preferably includes at least one main unit configured to communicate over a communications network such as, for example, a local area network, a wide area network, a wireless network (radio frequency, microwave, satellite, electromagnetic radiation, or the like) or a communications network that consists of any combination of the foregoing. The computer system may be connected to the communications network through any possible means such as, for example, cable, fiber, digital subscriber line (DSL), plain old telephone service (POTS), or the like. The main unit may include at least one processor (CPU) capable of running instrument control and data storage/management software, connected to a memory system including various memory devices, such as random access memory RAM, read only memory ROM, and one or more databases. The one or more databases may be local or remote; they may be located all on one computer system or distributed among more than one computer system; they may be kept both locally and remotely; they may also be maintained in such a manner that a master database or databases is/are maintained while copies are distributed to remote locations and updated according to the specific requirements of the particular implementation.

The computer system may be a general purpose computer system that is programmable using one or more computer programming languages (e.g., C, C++, Java, Visual Basic) and/or other languages (e.g., scripting languages like Perl, Active Server Pages, and/or Java Server Pages) or even assembly language. The computer system may also be specially programmed, special purpose hardware, or an application specific integrated circuit (ASIC).

In a general purpose computer system, the processor is typically a commercially available microprocessor, such as a Pentium series processor available from Intel, or other similar commercially available processor. Such a microprocessor executes a program called an operating system, such as UNIX, Linux, MacOS, BeOS, Solaris, Windows NT, Windows 95, 98, or 2000, or any other commercially available operating system, which controls the execution of other computer programs and provides scheduling, debugging, input/output control, user interface management, accounting, compilation, storage assignment, data management, memory management, network services, communication control and related services, and many other functions.

The processor may also execute additional infrastructure programs and/or services integrated with the operating system. These additional infrastructure programs could include commercially available instrument control and/or data storage/management solutions, an integration of commercially available software that can form the services of the instrument's control system, application servers, web servers, scripting engines, firewall servers and the like.

Still yet another alternative may be to provide a computer program, or collection of computer programs, which can be distributed separately on one or more computer-readable storage medium for installation on one or more computer systems forming an instrument control and data storage/management system. The distributed program or programs can be adapted to run on a computer or group/network of computers comprising an existing instrument control and/or data management/storage system that can process assay plates. For example, the program, or programs, may consist of a set of instructions which modify, alter, or enable an existing instrument control and/or data management/storage system to process plates in accordance with the present invention. Such a distributed program or programs may be stand-alone programs or may be software components or libraries which are easily integrated into and used by an existing instrument control and/or data storage/management system through a series of routine calls to services exposed by the components or libraries. The invention is not limited to implementations discussed above and therefore it should be understood that the particular implementation may take on many different forms depending on the particular requirements of the instrument control and/or data storage/management system, the detection subsystem, the plate handling subsystem the fluidic handling subsystem, the software running the one or more of the various subsystems, front/back-office software (Lab Data Management Systems, and the like) and the type of computer equipment employed.

As is generally understood in the art, an application server may include software which provides a consistent framework for the overall structure of programs for any application, in this case an instrument control and/or data storage/management system. An application server may provide services supporting database persistence to multiple different database technologies, process management, security, authentication, threading and thread-safe operation, server process hosting, remote communication, object naming, event handling, asynchronous and synchronous messaging, and many other services. The application server infrastructure could be based on CORBA, COM/DCOM, COM+, Enterprise Java Beans (EJB), and/or any other technology that provides infrastructure supporting the development of applications on an operating system. Example of application servers includes but is not limited to WebLogic from BEA Systems, WebSphere from IBM, Orbix from Iona Technologies, and COM+ from Microsoft.

The processor, operating system, and additional infrastructure software may be used as a computer platform for which application programs in high-level programming languages are written.

The database may be any kind of database, including a relational database, object-oriented database, unstructured database, multi-dimensional database, time-series database or other database. Example relational databases include Oracle 8I from Oracle Corporation of Redwood City, Calif.; Informix Dynamic Server from Informix Software, Inc. of Menlo Park, Calif.; DB2 from International Business Machines of Yorktown Heights, N.Y.; and Access from Microsoft Corporation of Redmond, Wash. An example of an object-oriented database is ObjectStore from Object Design of Burlington, Mass. An example of a time-series database for financial applications is TimeSquared from Saliton Associates of Toronto, Canada. An example of an unstructured database is Notes from the Lotus Corporation, of Cambridge, Mass. A database also may be constructed using a flat file system, for example by using files with character-delimited fields, such as in early versions of dBASE, now known as Visual dBASE from Inprise Corp. of Scotts Valley, Calif., formerly Borland International Corp.

The main unit may optionally include or be connected to an output device configured to provide information to a user. Example output devices include cathode ray tube (CRT) displays, liquid crystal displays (LCD) and other video output devices, printers, communication devices such as modems, storage devices such as a magnetic disk, optical disk, magneto-optical disk, tape, or the like, and audio or video output devices. Likewise, one or more input devices may be included with or connected to the main unit and configured to enable a user to input information to the main unit. Example input devices include a keyboard, keypad, track ball, mouse, pen and tablet, voice-control device, communication device, and data input devices such as audio and video capture devices. It should be understood that the invention is not limited to the particular input or output devices used in combination with the computer system or to those described herein.

It also should be understood that the invention is not limited to a particular computer platform, particular processor, or particular high-level programming language. Additionally, the computer system may be a multiprocessor computer system, a massively parallel computer system or may include multiple computers connected over a computer network and configured to perform parallel processing and/or distributed processing. It further should be understood that each module or step shown in the accompanying figures and the substeps or subparts may correspond to separate modules of a computer program, or may be separate computer programs. Such modules may be operable on separate computers. The data produced by these components may be stored in a memory system or transmitted between computer systems.

Such a system may be implemented in software, hardware, or firmware, or any combination thereof. Additionally, the system is not necessarily static but may be dynamically reprogrammed or reconfigured, either manually or automatically through some form of artificial intelligence or expert-based system, as those terms are currently understood. The various elements of the method for flexibly representing and processing assay plates disclosed herein, either individually or in combination, may be implemented as a computer program product tangibly embodied in a machine-readable storage device or medium for execution by the computer processor. Various steps of the process may be performed by the computer processor executing the program tangibly embodied on a computer-readable medium to perform functions by operating on input and generating output. Computer programming languages suitable for implementing such a system include procedural programming languages, object-oriented programming languages, and combinations of the two.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims.

What is claimed is:

1. A computerized instrument control and data storage/management system for representing an assay plate having one or more predefined plate locations having at least one central processing unit (CPU), and at least one memory storage device having stored therein a set of instrument control and data storage/management instructions for execution by the at least one CPU, the set of instrument control and data storage/management instructions providing, when so executed, at least one instrument with the ability to represent the assay plate, the set of instrument control and data storage/management instructions comprising:

a first set of instructions constructed and arranged to access a database comprising a plate type directory, which comprises a plurality of graph data structures and represent the assay plate as a graph data structure of the plurality of graph data structures, wherein the graph data structure comprises a node for each of the one or more predefined plate locations, and the node is hierarchically arranged to correspond to the physical structure of a first assay plate;

a second set of instructions constructed and arranged to store at least one data object associated with the assay plate, wherein the at least one data object comprises one or more data records, and the at least one data object is not stored on a database comprising the graph data structure; and a third set of instructions constructed and arranged to access at least one layer object to map the at least one data object to one or more nodes within the graph data structure representation of the assay plate, at least one instrument with the ability to process a physical assay plate that corresponds to the first assay plate;

the physical assay plate, wherein the system is further configured to process the physical assay plate, wherein the set of instrument control and data storage/management instructions provide, when so executed, the at least one instrument with the additional ability to process the physical assay plate, the set of instrument control and data storage/management instructions further comprising one or more additional sets of instructions constructed and arranged to configure an assay system to process the physical assay plate, and wherein the one or more additional sets of instructions are constructed and arranged to (a) read one or more plate processing files from the at least one memory storage device;
(b) determine a plate type of the physical assay plate;
(c) select a plate processing file from the one or more plate processing files that correspond to the plate type;
(d) configure the at least one instrument to process the physical assay plate in accordance with the selected plate processing file;
(e) process the physical assay plate, creating processed data; and
(f) associate the processed data with the one or more nodes within the graph data structure.

2. The system of claim 1 wherein the physical assay plate has a predefined number of wells arranged in a plurality of well groupings, and wherein the one or more predefined plate locations include: one or more spots in each well; and one or more sectors associated with each grouping of wells, wherein the one or more sectors each contain the one or more spots, respectively, from each well of the associated group of wells.

3. The system according to claim 1, each node having a unique node identified and a node type.

4. The system according to claim 3, wherein the node type includes one of a plate, sector, well or spot.

5. The system according to claim 4, each of the at least one layer objects having an index, wherein the index maps each node identifier to one or more of the at least one data objects.

6. The system according to claim 1, wherein the graph data structure is a tree data structure.

7. The system according to claim 2, wherein the physical assay plate comprises 96 wells arranged in a grid of 8 rows and 12 columns of wells, wherein each well grouping is one column of wells.

8. The system according to claim 1, wherein the physical assay plate has associated geometry data that includes one or more predefined points of interest, the system further comprising: a tree of one or more multi-dimensional coordinate space objects having a plurality of subspaces, the subspaces each being anchored in the coordinate space object at a predefined subspace anchor point, wherein one or more of the plurality of subspaces may contain one or more of the predefined points of interest.

9. The system of claim 1, wherein the hierarchical containment relationships include three or more hierarchies of containment.

10. The system of claim 1 wherein the one or more additional sets of instructions further comprise one or more supplemental sets of instructions constructed and arranged to associate assay results obtained from processing the physical assay plate with one or more nodes of the one or more predefined plate locations.

11. A non-transitory computer readable medium having stored thereon a computer program which, when executed on a computing system operatively connected to an assay system, causes the assay system to perform a method for flexibly representing an assay plate, the method comprising the steps of:

accessing a database comprising a plate type directory, which comprises a plurality of graph data structures and representing the assay plate in a graph data structure of the plurality of graph data structures, wherein the graph data structure comprises a node for each of the one or more predefined plate locations and said node is hierarchically arranged to correspond to the physical structure of a first assay plate;

storing a least one data object having one or more data records, wherein the at least one data object is associated with the assay plate and the at least one data object is not stored on a database comprising the graph data structure; and mapping the at least one data object to one or more nodes within the graph data structure via at least one layer object, accessing at least one instrument with the ability to process a physical assay plate that corresponds to the first assay plate;

accessing the physical assay plate, wherein the system is further configured to process the physical assay plate, wherein the set of instrument control and data storage/management instructions provide, when so executed, the at least one instrument with the additional ability to process the physical assay plate, the set of instrument control and data storage/management instructions further comprising one or more additional sets of instructions constructed and arranged to configure the assay system to process the physical assay plate, and process the physical assay plate, and wherein the one or more additional sets of instructions are constructed and arranged to (a) read one or more plate processing files from the at least one memory storage device;
(b) determine a plate type of the physical assay plate;
(c) select a plate processing file from the one or more plate processing files that correspond to the plate type;
(d) configure the at least one instrument to process the physical assay plate in accordance with the selected plate processing file;
(e) process the physical assay plate, creating processed data; and
(f) associate the processed data with the one or more nodes within the graph data structure.

12. The computer readable medium according to claim 11, wherein the physical assay plate has a predefined number of wells arranged in a plurality of well groupings, and wherein the one or more predefined plate locations include: one or more spots in each well; and one or more sectors associated with each grouping of wells, wherein the one or more sectors each contain the one or more spots, respectively, from each well of the associated group of wells.

13. The computer readable medium according to claim 11, wherein each node has a unique node identifier and a node type.

14. The computer readable medium according to claim 13, wherein the node type includes a plate, sector, well or spot.

15. The computer readable medium according to claim 11, wherein each of the at least one layer objects comprises an index, wherein the index maps each node identifier to one or more of the at least one data objects.

16. The computer readable medium according to claim 11, wherein the graph data structure is a tree data structure.

17. The computer readable medium according to claim 12 wherein the physical assay plate comprises 96 wells arranged in a grid of 8 rows and 12 columns of wells, wherein each well grouping is one column of wells.

18. The computer readable medium according to claim 12, wherein the physical assay plate has associated geometry data that includes one or more predefined points of interest, the system further comprising: a tree of one or more multi-dimensional coordinate space objects having a plurality of subspaces, the subspaces each being anchored in the coordinate space object at a predefined subspace anchor point, wherein one or more of the plurality of subspaces may contain one or more of the predefined points of interest.

19. The computer readable medium according to claim 11, wherein the hierarchical containment relationships include three or more hierarchies of containment.

20. The computer readable medium according to claim 11 wherein said computer readable medium comprises said plate type directory comprising said graph data structure.

* * * * *